United States Patent
Campanatti, Jr. et al.

(10) Patent No.: US 10,140,888 B2
(45) Date of Patent: Nov. 27, 2018

(54) TRAINING AND TESTING SYSTEM FOR ADVANCED IMAGE PROCESSING

(71) Applicant: TERARECON, INC., Foster City, CA (US)

(72) Inventors: Gelson Campanatti, Jr., Sao Paulo (BR); Vishal Chodnekar, Foster City, CA (US); Sha He, Belmont, CA (US); Robert James Taylor, San Francisco, CA (US)

(73) Assignee: TeraRecon, Inc., Foster City, CA (US)

( * ) Notice: Subject to any disclaimer, the term of this patent is extended or adjusted under 35 U.S.C. 154(b) by 270 days.

(21) Appl. No.: 13/801,583

(22) Filed: Mar. 13, 2013

(65) Prior Publication Data

US 2014/0087342 A1    Mar. 27, 2014

Related U.S. Application Data

(60) Provisional application No. 61/703,932, filed on Sep. 21, 2012.

(51) Int. Cl.
| | |
|---|---|
| G09B 23/28 | (2006.01) |
| G09B 23/00 | (2006.01) |
| G06F 19/00 | (2018.01) |

(52) U.S. Cl.
CPC .......... G09B 23/28 (2013.01); G06F 19/321 (2013.01); G09B 23/00 (2013.01)

(58) Field of Classification Search
USPC ........................................................ 434/262
See application file for complete search history.

(56) References Cited

U.S. PATENT DOCUMENTS

| | | | |
|---|---|---|---|
| 5,529,498 A * | 6/1996 | Cassily et al. | 434/258 |
| 7,693,317 B2 * | 4/2010 | Vining et al. | 382/128 |
| 2009/0204426 A1 * | 8/2009 | Thorne et al. | 705/2 |
| 2010/0005413 A1 * | 1/2010 | Liang et al. | 715/781 |

(Continued)

FOREIGN PATENT DOCUMENTS

| | | |
|---|---|---|
| WO | WO 2009/106784 | 9/2009 |
| WO | WO 2010/111305 | 9/2010 |

OTHER PUBLICATIONS

International Search Report and Written Opinion dated Dec. 10, 2013, for International Patent Application No. PCT/US2013/060557, 12 pages.

(Continued)

*Primary Examiner* — James Hull
(74) *Attorney, Agent, or Firm* — Douglas L. Weller

(57) ABSTRACT

Techniques for providing medical image processing training are described herein. According to one embodiment, at least one medical image associated with a medical image processing training course (MIPTC) is displayed in a first display area. An instruction is displayed in a second display area, where the instruction requests a user to perform a quantitative determination on at least a portion of a body part within the medical image displayed in the first display area. In response to a user action from the user, the requested determination is performed on the displayed medical image. It is determined automatically without user intervention at least one quantitative value representing a result of the user action. The quantitative value is compared to a predefined model answer.

27 Claims, 28 Drawing Sheets

(56) References Cited

U.S. PATENT DOCUMENTS

| | | | | |
|---|---|---|---|---|
| 2012/0170820 A1* | 7/2012 | Declerck et al. | ............. | 382/128 |
| 2012/0257804 A1* | 10/2012 | Zhang | .................... | A61B 6/563 |
| | | | | 382/128 |
| 2013/0065211 A1* | 3/2013 | Amso | ..................... | G09B 9/00 |
| | | | | 434/262 |

OTHER PUBLICATIONS

Luursema, J. M. et al., "Optimizing conditions for computer-assisted anatomical learning," Interacting with Computers, Butterworth-Heinemann, Great Britain, vol. 18, No. 5, Sep. 1, 2006, pp. 1123-1138.

Ashwell, Ken W. S. et al, "An Acrobat-based program for gross anatomy revision," Medical Education, vol. 38, No. 11, Nov. 1, 2004, pp. 1185-1186.

Shaffer K. et al., "Blended learning in medical education: Use of an integrated approach with web-based small group modules and didactic instruction for teaching radiologic anatomy," Academic Radiology, Reston, VA, US, vol. 11, No. 9, Sep. 1, 2004, pp. 1059-1070.

Nivala, Markus et al., "Using virtual microscopy to scaffold learning of pathology: a naturalistic experiment on the role of visual and conceptual cues," Instructional Science; An International Journal of the Learning Sciences, Kluwer Academic Publishers, DO, vol. 40, No. 5, Mar. 30, 2012, pp. 799-811.

PCT Notification concerning Transmittal of International Preliminary Report on Patentability (Chapter I of the Patent Cooperation Treaty) for PCT Counterpart Application No. PCT/US2013/060557, 8 pgs., (dated Apr. 2, 2015).

\* cited by examiner

TRAINING AND TESTING SYSTEM FOR ADVANCED IMAGE PROCESSING

RELATED APPLICATIONS

This application claims the benefit of U.S. Provisional Patent Application No. 61/703,932, filed Sep. 21, 2012, which is incorporated by reference herein in its entirety.

FIELD OF THE INVENTION

Embodiments of the present invention relate generally to medical image processing. More particularly, embodiments of the invention relate to providing medical image processing training.

BACKGROUND

A computerized axial tomography scan (commonly known as a CAT scan or a CT scan) is an x-ray procedure, which combines many x-ray images with the aid of a computer to generate cross-sectional views of the internal organs and structures of the body. In each of these views, the body image is seen as an x-ray "slice" of the body. Typically, parallel slices are taken at different levels of the body, i.e., at different axial (z-axis) positions. This recorded image is called a tomogram, and "computerized axial tomography" refers to the recorded tomogram "sections" at different axial levels of the body. In multislice CT, a two-dimensional (2D) array of detector elements replaces the linear array of detectors used in conventional CT scanners. The 2D detector array permits the CT scanner to simultaneously obtain tomographic data at different slice locations and greatly increases the speed of CT image acquisition. Multi-slice CT facilitates a wide range of clinical applications, including three-dimensional (3D) imaging, with a capability for scanning large longitudinal volumes with high z-axis resolution.

Magnetic resonance imaging (MRI) is another method of obtaining images of the interior of objects, especially the human body. More specifically, MRI is a non-invasive, non-x-ray diagnostic technique employing radio-frequency waves and intense magnetic fields to excite molecules in the object under evaluation. Like a CAT scan, MRI provides computer-generated image "slices" of the body's internal tissues and organs. As with CAT scans, MRI facilitates a wide range of clinical applications, including 3D imaging, and provides large amounts of data by scanning large volumes with high resolution.

Medical image data, which are collected with medical imaging devices, such as X-ray devices, MRI devices, Ultrasound devices, Positron Emission Tomography (PET) devices or CT devices in the diagnostic imaging departments of medical institutions, are used for an image interpretation process called "reading" or "diagnostic reading." After an image interpretation report is generated from the medical image data, the image interpretation report, possibly accompanied by representative images or representations of the examination, are sent to the requesting physicians. Today, these image interpretation reports are usually digitized, stored, managed and distributed in plain text in a Radiology Information System (RIS) with accompanying representative images and the original examination stored in a Picture Archiving Communication System (PACS) which is often integrated with the RIS.

Typically, prior to the interpretation or reading, medical images may be processed or rendered using a variety of imaging processing or rendering techniques, using advanced image processing software. Advanced image processing software is complicated, powerful and complex. A patient's health and sometimes life may depend on its being used correctly. As a result, learning to use the software effectively is neither a trivial nor a simple task.

Training to use advanced image processing software is currently done manually. For example an instructor and several students in a classroom may each have access to a workstation connected to a common server. The instructor and students can access the same cases that are stored in a database on the server. The instructor may have read the cases or have knowledge of the clinical outcomes of the cases before coming into the classroom, and may have jotted down notes relating to quantitative data, measurements, or screenshots relating to the case. The instructor may also have stored scenes relating to the cases in his computer.

The instructor's workstation may be connected to a projector so the students can see his computer as he works on the cases. This may happen before or after the students attempt to read the cases on their own. The students can manually compare their screen to the instructor's screen. Measurements, quantitative data etc. that the students have extracted from the cases can be compared manually to those of the instructor. For example, the instructor may read out loud that his measurement of an artery diameter was 2 millimeters (mm). The students can then see how close they came to that measurement in their evaluation of the case.

The instructor doesn't have a good way of monitoring the students' progress, except perhaps, by walking around the classroom. He also doesn't have a good way of grading or testing the students unless he physically monitors each student's work. Because the entire class has to do the same case at the same time, some students must wait for others to complete the case. Some may not feel they have enough time to complete the case in the allotted time period. It would be desirable to have a training system that is integrated with an advanced image processing software system so that the process of training users on the advanced image processing software were more automated and effective than the manual system used now.

BRIEF DESCRIPTION OF THE DRAWINGS

Embodiments of the invention are illustrated by way of example and not limitation in the figures of the accompanying drawings in which like references indicate similar elements.

DETAILED DESCRIPTION

Figure 1:
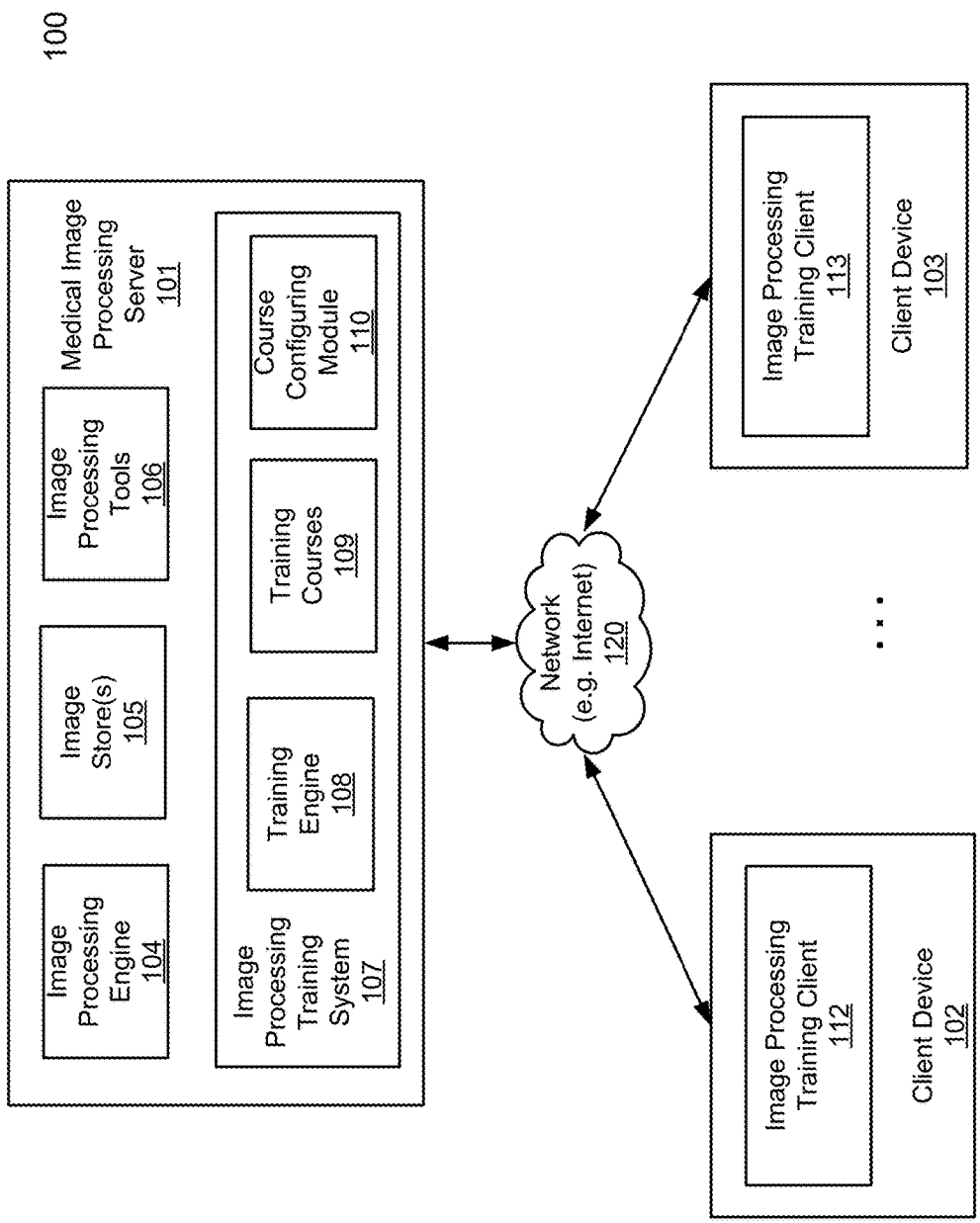
FIG. 1 is a block diagram illustrating an advanced imaging processing system according to one embodiment.

Various embodiments and aspects of the inventions will be described with reference to details discussed below, and the accompanying drawings will illustrate the various embodiments. The following description and drawings are illustrative of the invention and are not to be construed as limiting the invention. Numerous specific details are described to provide a thorough understanding of various embodiments of the present invention. However, in certain instances, well-known or conventional details are not described in order to provide a concise discussion of embodiments of the present inventions.

Reference in the specification to "one embodiment" or "an embodiment" means that a particular feature, structure, or characteristic described in conjunction with the embodiment can be included in at least one embodiment of the invention. The appearances of the phrase "in one embodiment" in various places in the specification do not necessarily all refer to the same embodiment.

According to some embodiments, an advanced image processing training and/or testing system is provided to provide a training platform to allow users to learn medical image processing techniques. Such a training platform is preferably provided over a network such as the Internet (e.g., a cloud-based system) in which a user (e.g., a student or an instructor) can use a thin client such as a Web browser to access or to provide a variety of medical image processing training courses. The platform may be hosted by one or more servers associated with an image processing engine that processes the medical images. Users may include medical doctors, medical technicians, students, medical insurance agents, and the like. The medical image processing tools may be the same as those used to process medical images in current practices such as hospital radiology departments or clinics, etc. Users may include medical doctors who perform diagnosis of patients' medical images, instructors who provide medical image processing training to students, and/or students or others. Different user interfaces may be used for different users using the same advanced image processing system depending upon the role or access privilege of the user. Similarly, the images used in a training course may be derived from the images used in the real clinical practices with confidential information such as patient information removed.

There are several benefits to advanced image processing training. An advanced image processing training course can provide the clinical methodology needed to interpret different types of clinical cases. The training can also help a student gain familiarity with the clinical tools used in real clinical evaluations. In addition, the training courses may familiarize the student with a particular software system that they are expected to use in their work. In addition, advanced image processing training can be used for accreditation, such as ACR (American College of Radiology), ACC (American College of Cardiology), CME (Continuing Medical Education), etc.

The advanced image processing training system can be utilized by at least two different users, the student and the instructor. A student may be a physician, a technician or other type of user. Similarly, an instructor may be a physician, technician or other type of user. Other users may also exist, such as an administrator. The advanced image processing training system may be used for training, quizzing, and/or testing the students in either a classroom or self-paced environment. Grading and/or scoring of the students can be done automatically, manually, or a combination of both. The interface for the student user and the instructor user are different, although they may have some overlap.

FIG. 1 is a block diagram illustrating an advanced imaging processing system according to one embodiment. Referring to FIG. 1, according to one embodiment, system 100 includes one or more clients 102-103 communicatively coupled to a medical imaging processing server 101 and over a network 120, wired and/or wirelessly. Network 120 may be a local area network (LAN), a metropolitan area network (MAN), a wide area network (WAN) such as the Internet or an intranet, a private cloud network, a public cloud network, or a combination thereof.

Medical imaging processing server 101 includes an image processing engine 104 which is configured to provide medical image processing services to clients 102-103 over a network. In one embodiment, the medical imaging processing server 101 also includes an image store 105 to store medical data such as digital imaging and communications in medicine (DICOM) compatible data or other image data, including jpeg, TIFF, video, EKG, laboratory images, portable document format (PDF), audio, and other files. The image store may also exist outside of the image processing server and be connected to the image processing server via a network or other means. The image store 105 may also incorporate encryption capabilities, where the medical data can be stored and transmitted in an encrypted form. The image store 105 may include one or more databases, and may be implemented with relational database management systems (RDBMS), e.g., Oracle™ database or Microsoft® SQL Server, etc. In one embodiment, the medical imaging processing server 101 includes an access control system (not shown) to control access, by the clients 102-103, of resources (e.g., image processing tools 106) and/or medical data stored in image store 105. Clients 102-103 may or may not have access to certain portions of resources and/or medical data stored in image store depending upon the access privileges of the user. The access privileges may be determined or configured based on a set of role-based rules or policies. For example, client 102 may be configured with certain roles (e.g., doctors and/or instructors) that only permit access to some of the tools and/or images/image data provided by the medical imaging processing server 101. In other instances, client 103 may be configured with certain roles (e.g., students) that limit its access to some patient information or other information. For example, certain users (e.g., doctors, medical students) of client 102 may have different access privileges to access different medical information stored in image store 105 or different imaging rendering resources provided by imaging processing server 101 or different user information such as test results, or other information.

Referring back to FIG. 1, according to one embodiment, client 102 further includes image processing training client software 112 (e.g., Web browser or thin client) to access training courses 109 provided by training engine 108 of image processing training system 107 over network 120. In one embodiment, image processing training client 112 displays training courses 109, which are provided by course configuring module 110, for example, using images from image stores 105. The user can follow the instructions provided by the courses to perform certain image processing operations, which will invoke image processing tools 106 to process the course images. The results of the image processing operations are compared, automatically, manually, or a combination of both, to model answers which are also provided by course configuring module 110 as part of the course. Image processing training system 107 may or may not be a part of medical image processing server 101. The two systems may be on the same machine, different machines and/or connected via a network.

Figure 2:
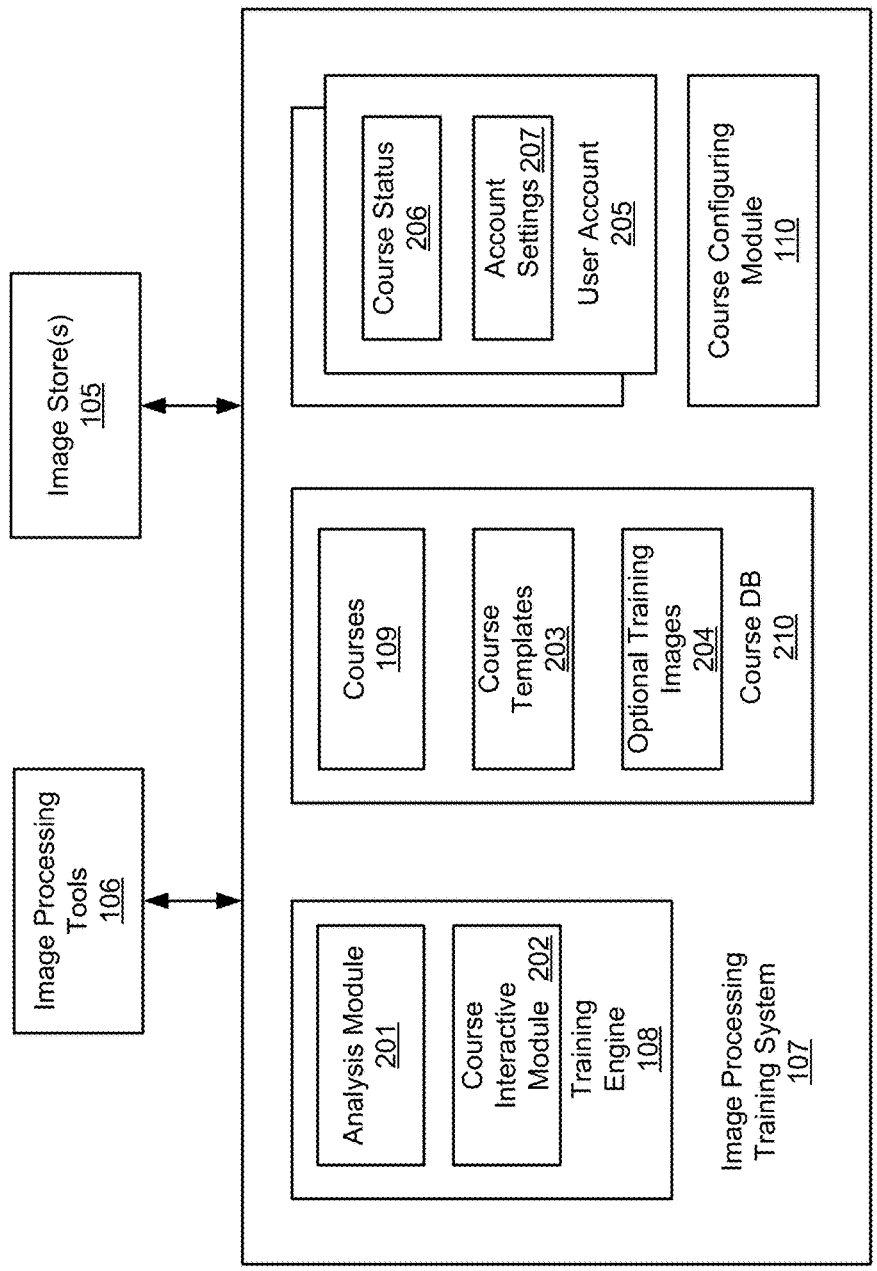
FIG. 2 is a block diagram illustrating an example of an image processing training system according to one embodiment of the invention.

FIG. 2 is a block diagram illustrating an example of an image processing training system according to one embodiment of the invention. Referring to FIG. 2, training engine 108 includes an analysis module 201 and course interactive module 202. Interactive module 202 is configured to interact with the trainee via the training courses. Analysis module 201 is for analyzing the trainees' participation results and training statistics. Image processing training system 107 further maintains a course database 210 to manage and store courses 109, including results, course templates 203, and optional training images 204. Courses 109 may be created and provided by course configuring module 110 using training images 204 and course templates 203. Courses may be created with or without the course templates. Also, the images may reside on a separate server, or in a separate location. For each use, whether a trainer or a trainee, a user account 205 is maintained to store the course status 206 associated with the user, as well as account and access settings 207 and possibly course results. Course status 206 may include information concerning in which courses the user has participated, the progress of each course, and history of the user's interactions with the course, results, etc. Account settings 207 may store information concerning the individual's settings such as the user type/privileges (e.g., doctor, trainer, trainee, etc.). For example, if a logged-in user is a trainer, the interface of course configuring module 110 becomes available to allow the user to create courses 109 using course templates 203 and training images 204. If the logged-in user is a trainee, the user may only have access to the courses 109 to which the user has subscribed and the user may not access course configuring module 110, nor course templates 203. Note that some or all of the components as shown in FIG. 2 may be implemented in software, hardware, or a combination thereof.

Figure 3:
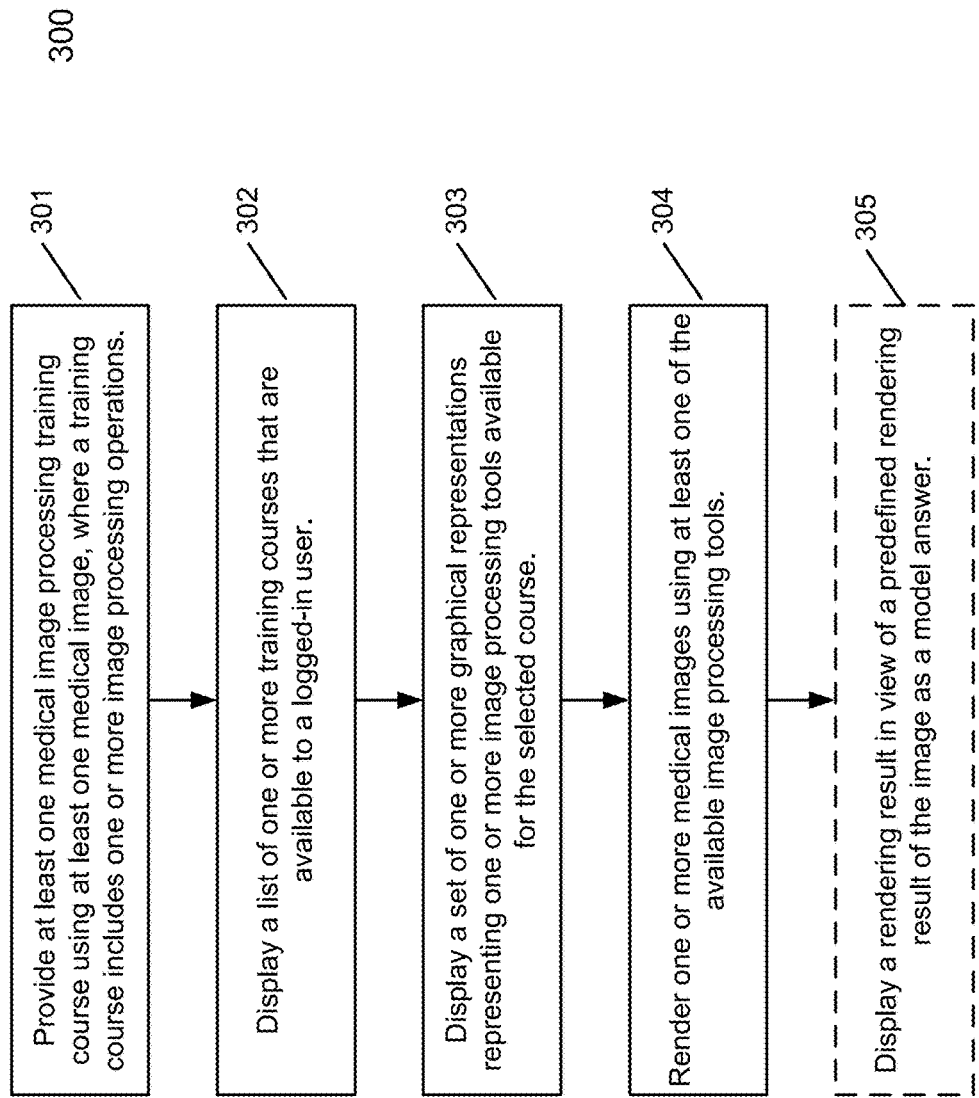
FIG. 3 is a flow diagram illustrating a method for providing medical image processing training according to one embodiment of the invention.

FIG. 3 is a flow diagram illustrating a method for providing medical image processing training according to one embodiment of the invention. For example, method 300 may be performed by image processing training system 107 of FIG. 2, which may include processing logic in software, hardware, or a combination thereof. Referring to FIG. 3, at block 301, at least one medical image processing training course is provided using at least one medical image. A training course includes one or more image processing operations. At block 302, processing logic displays a list of one or more training courses that are available to the logged-in user. At block 303, a list of one or more graphical representations representing at least one image processing tool that is available for the selected course is displayed. Alternatively, a question may be presented requesting a user to perform certain action (e.g., identification of a body part), without requiring actual image processing operations. At block 304, in response to a prompted instruction, one or more images are rendered using one or more of the available tools. At block 305, the results may be displayed in view of the predefined results (e.g., model answers) of the question which may be displayed instantly and automatically.

Figure 4A:
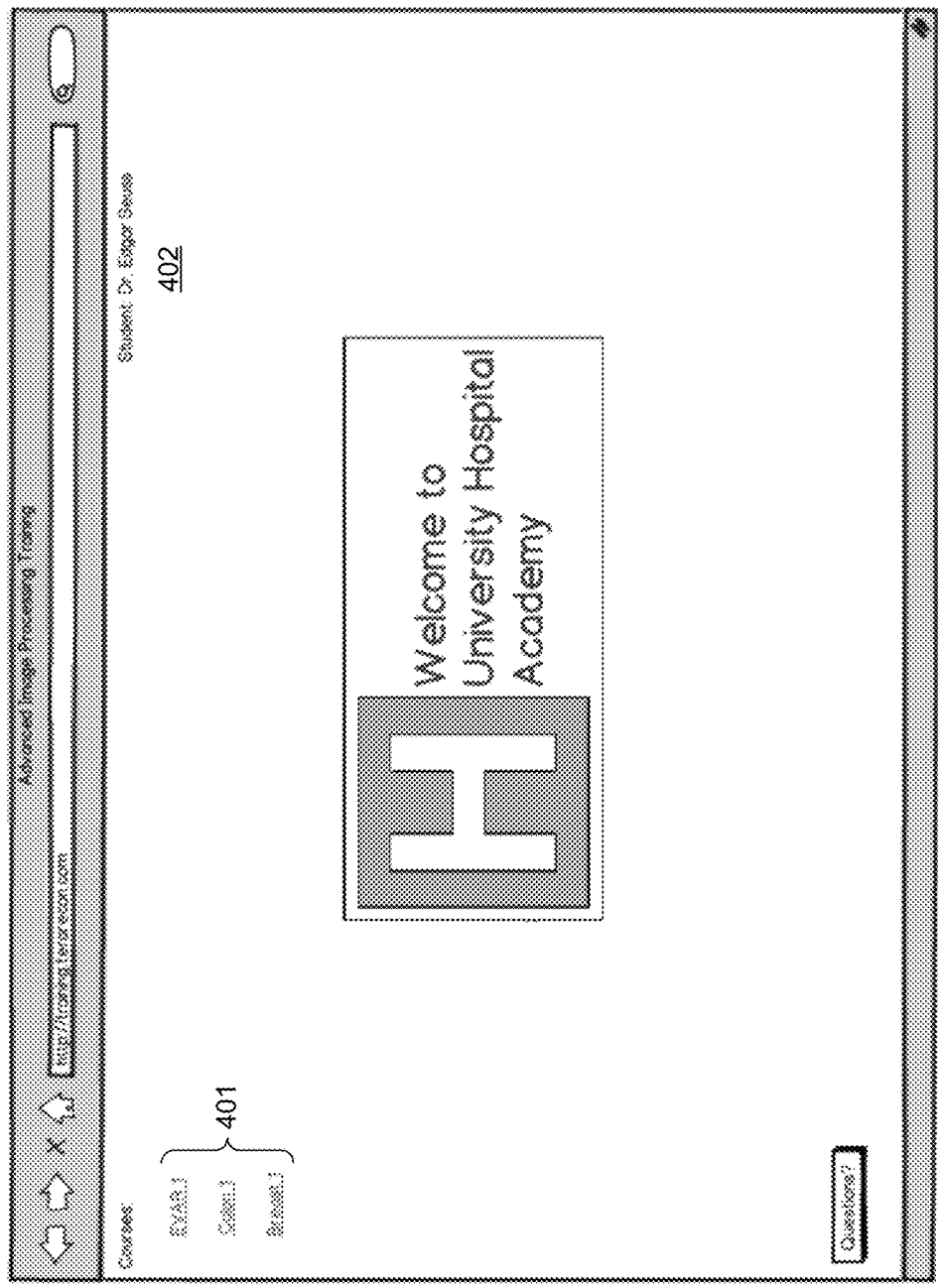
FIGS. 4A-4I are screenshots representing examples of graphical user interfaces of a medical image processing training system according to certain embodiments of the invention.

FIGS. 4A-4I are screenshots representing examples of graphical user interfaces of a medical image processing training system according to certain embodiments of the invention. The graphical user interfaces (GUIs) as shown in FIGS. 4A-4I may be presented by image processing training system 107 of FIGS. 1-2. Referring to FIGS. 4A-4I, when a user, in this example a trainee, logs into medical image processing training system 107, a list of one or more courses 401 that are available to the user, as well as a trainee identifier 402 are displayed as shown in FIG. 4A.

The courses listed 401, may be determined by payment, qualifications (possibly determined by experience, education or prerequisites), assignment etc. The courses may be organized by level, specialty, procedure or other ways. Courses 401 may be listed that the student is not yet qualified to take, for example, the courses 401 may list "Colon 1" and "Colon 2". In this situation, when the student clicks on "Colon 2", when the student has not yet taken Colon 1, and if Colon 1 is a prerequisite for Colon 2, the student will get a message saying as much. Courses which have already been taken may be available to be taken again.

If the student was in the middle of taking a course when he last logged off the system, the system may bypass the course listing screen and take the student directly to the place in the course where he logged off. The student may also get a notice asking him if he wants to go back to his course in progress. A student's login information may be controlled by the instructor or other administrator. The student may also determine his own login information through a process of registration.

Figure 4B:
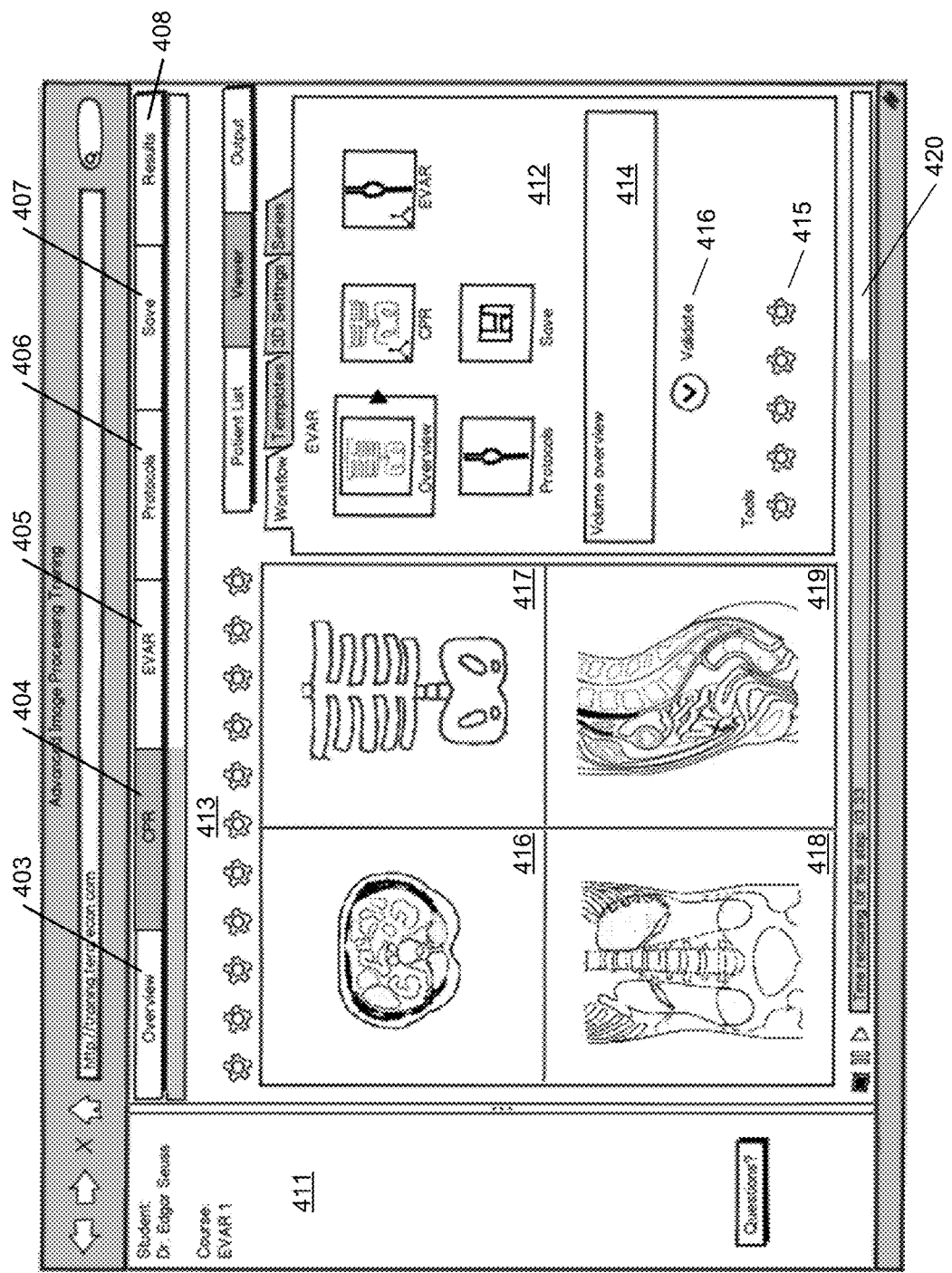

Once the student clicks on a particular course, he is brought to the main course screen (or told he does not have access, if he does not for some reason), as shown in FIG. 4B. The main course screen as shown in FIG. 4B may show the different steps that are to be taken during the selected course, in this example, Endovascular Aortic Repair (EVAR) 1. Alternatively, the course screen may show only the first step, and show the subsequent steps only when the previous step is completed. The steps for each course may be the same across courses or specific to the course. In this example, several pages of the selected course are displayed, including overview 403, Curved Planar Reformation (CPR) 404, EVAR 405, protocols 406, save 407, and results 408. The course steps may be labeled in other ways also, for example "step 1", "step 2", etc.

In one embodiment, the GUI as shown in FIG. 4B includes a first display area 411 to display the currently selected course and the trainee's identifier, a second display area 412 to display course detailed information of the selected course, and a third display area 413 to display one or more medical images associated the selected course. In one embodiment, display area 412 includes a workflow page defining a workflow having one or more workflow stages associated with the course. Display area 412 may also show one or more graphical representations representing one or more image processing tools.

In one embodiment, a workflow is defined to capture the repetitive pattern of activities in the process of medical diagnosis, such as various image generation operations. A workflow arranges these activities into a process flow according to various factors, such as each activity's order, functions, resources requirements, and outputs, etc. Each activity in a workflow is called a workflow stage. Thus, a workflow stage, also referred to as a workflow element, captures various details of an activity, such as the activity's function, inputs received, and outputs generated, etc.

In one embodiment, a workflow template is created for a specific type of medical diagnosis or processing. A workflow template is a template with a predefined set of workflow stages. Each workflow stage in the workflow template includes one or more image processing operations. These image processing operations receive medical image data collected by medical imaging devices, such as scanners, as inputs, process the medical image data, and generate metadata as outputs. Metadata, also known as metadata elements, broadly refers to parameters and/or instructions for describing, processing, and/or managing the medical image data. For instance, metadata generated by the image processing operations of a workflow stage includes image processing parameters that can be applied to medical image data to generate medical image views for diagnostic purpose. Further, various automatic and manual manipulations of the medical image views can also be captured as metadata. Thus, metadata allows the returning of the system to the state it was in when the metadata was saved.

In another embodiment, a user selects one previously created workflow template and applies it to a set of medical image data for a specific medical study. Alternatively, a default workflow template may be provided to the user automatically based on the macro anatomy of the medical image data and/or the identity of the user. For example, a particular user (e.g., a radiologist) may set a certain predefined cardiac workflow template as the user's default workflow template for cardiac scans. The application of the workflow template to the medical image data creates a workflow scene. A workflow scene is an entity for tracking the progression of, and for recording the results of, processing through a workflow. Once created, the workflow scene contains the same workflow stages as defined in the workflow template it is created from. A user can follow the workflow logic as defined in the workflow scene, and proceed to a next workflow stage after finishing one, without the presence of the workflow template. Thus, for any given workflow scene, the user can quickly grasp its current processing status and its remaining workflow stages that need to be performed.

A workflow scene also contains a collection of scenes for storing results generated from the processed workflow stages. A scene contains metadata generated from one workflow stage. The metadata in the scene is generated by the image processing operations of the workflow stage, when applying to the medical image data to produce a set of medical image views. Once a workflow stage is completed, the resulted scene can be added into the collection of scenes in the workflow scene. Thus, the collection of scenes provides a history of what have been performed in one workflow scene.

In one embodiment, a scene can be applied to the medical image data to reproduce the set of medical image views. When reviewing the medical image views reproduced from a scene, a user may adjust these image views by making updates to the image processing parameters (metadata) contained in the scene. Afterwards, the updated image processing parameters can be saved to the scene to replace the previously stored image processing parameters. The newly updated scene can also be stored in the workflow scene to replace the old scene. Alternatively, a new series of workflow scene can be independently maintained to store one route of processing the medical image data through the workflow.

In some embodiments, a workflow template may be user-created for processing a specific type of medical image data. The user could add either predefined workflow stages, or customized workflow stages, to the workflow template. When processing a sample medical image data, the manual adjustments and configurations during the processing can be recorded and stored as image processing operations into a customized workflow stage. The customized workflow stage can then be applied to other medical image data to perform the same image processing operations as recorded during the workflow stage creation.

In some embodiments, a workflow scene is automatically generated by a preprocessor based on a workflow template. Since a workflow template contains predefined workflow stages with information on how to process, and the order of processing, medical image data, the preprocessor could utilize the workflow template to start the automated processing as soon as the medical image data is collected and made available. Alternatively, the preprocessor could automatically generate scenes for a workflow scene. A user may accept, or make minor updates to the auto-generated scenes when reviewing the workflow scene. Further detailed information concerning workflow templates can be found in co-pending U.S. patent application Ser. No. 12/196,099, entitled "Workflow Template Management for Medical Image Data Processing," filed Aug. 21, 2008, which is incorporated by reference herein in its entirety. The workflow stages of a workflow template may correspond to training steps in image processing training system 107.

Referring back to FIG. 4B, in this example, the workflow stages are displayed in a form of thumbnail images or icons in display area 412. When a user selects one of the workflow stages, in this example, the "Overview" stage, one or more medical images, in this example, images 416-419, which have been associated with the course and selected workflow stage are displayed in display area 413. In addition, an instruction box or area 414 is displayed to show a command or an instruction to prompt the trainee to perform a predetermined image processing operation. The instruction may be provided by a trainer during the configuration phase of the course. Based on the instruction provided through instruction box 414, the user can perform the required image processing operations using at least one of the image processing tools represented by graphical representations or icons 415. Once the image processing operations have been performed, the user can validate the current step by activating validation button 416. Note that some steps may not involve image processing tools.

Figure 4C:
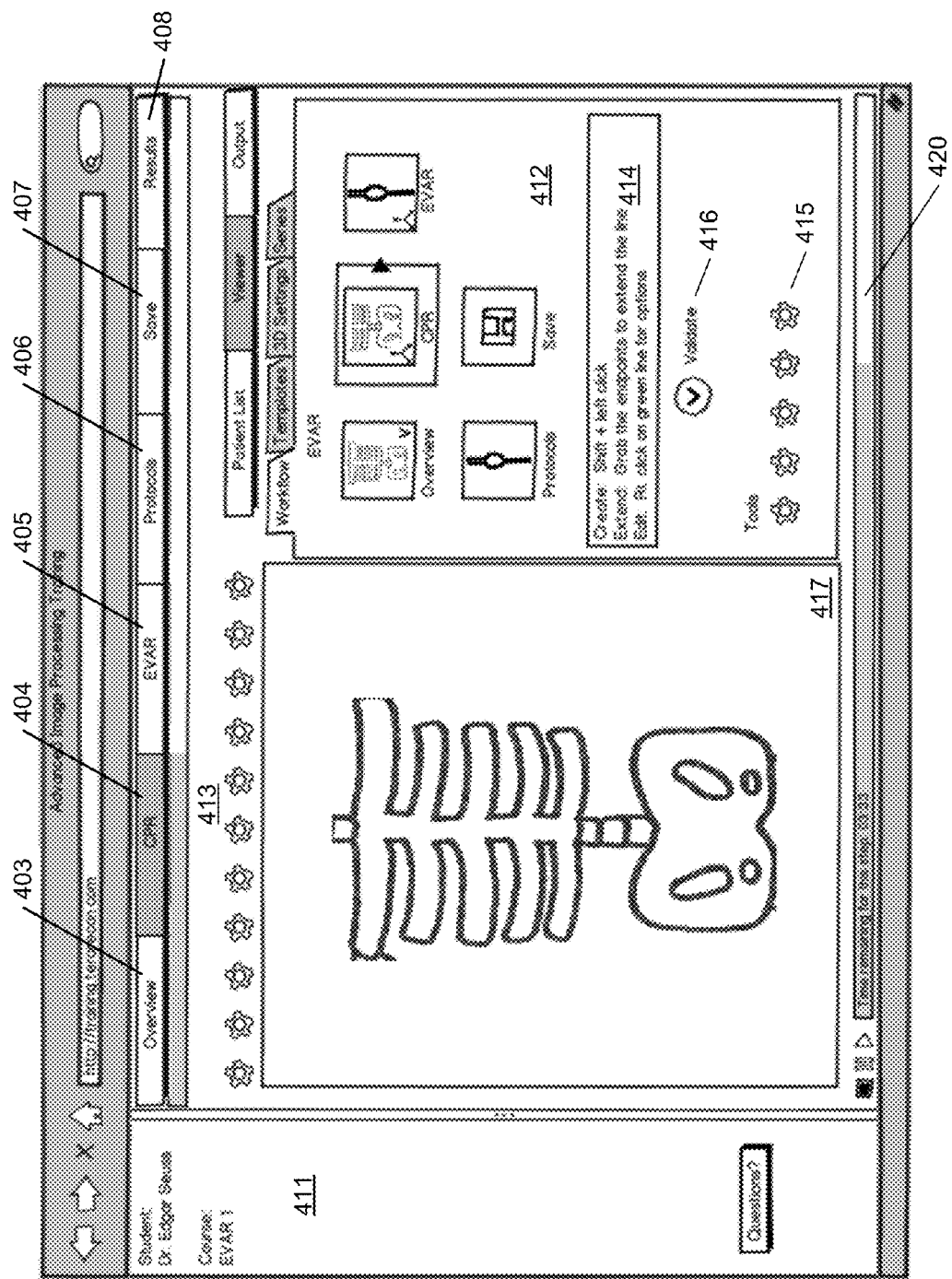

Once a step is validated, saved, or the next step is selected, a further detailed training course page is displayed as shown in FIG. 4C. FIG. 4C shows a screen for advanced image processing relating to endovascular aortic repair (EVAR). The steps shown here are overview 403, CPR (Curved Planar Reformation) 404, EVAR 405, Protocols (where one chooses a stent manufacturer and performs the appropriate measurement protocols) 406, Save 407, and results 408. A progress bar or timeline 420 is displayed showing the student's progress within the course may be shown, either in percentage or in time units. In this example, the student is on the second step, CPR 404. The student performs the necessary operations specified by the instruction provided in instruction box 414 within each step and then advances to the next step by pressing a "next", "save" or "validate" or any other appropriate button, key or link. The training system may or may not allow the student to go back and repeat or redo steps. This option may be set by the instructor and may be displayed as part of instruction displayed in instruction box 414. If required information is not present when the student attempts to advance to the next step, an error message may be generated to inform the student. Courses can be very dynamic in nature, requiring the user to go back and forth among the steps. If the student is allowed to go back and forth among the steps, his current location may be identified on the progress bar.

Each step or all the steps may have a time limit, or the training system may simply track the time to perform each or all the steps. The student may be able to pause the course, or stop the course, and come back to it at a later time. If the course is paused, the screen may change to a blank or set screen so that the student cannot continue to visually study the course screen without being timed. As the student progresses through the course, he may be asked to enter different information. For example, the student may be asked to manipulate the image on the screen (rotate it, change the view, remove organs, zoom in or out, etc.) and to save a screenshot, or scene, of the study. This scene may be available later to the instructor to evaluate. Similarly, the student may be asked to take measurements, locate anatomy, segment anatomy, answer questions etc. The questions may be in a variety of forms such as free text form, radio button, or checkbox. The student may be asked to make a diagnosis. Instructions for each step of the course may be included in instruction box 414. All this information may be stored for grading and/or evaluation by the instructor and/or student.

Figure 4D:
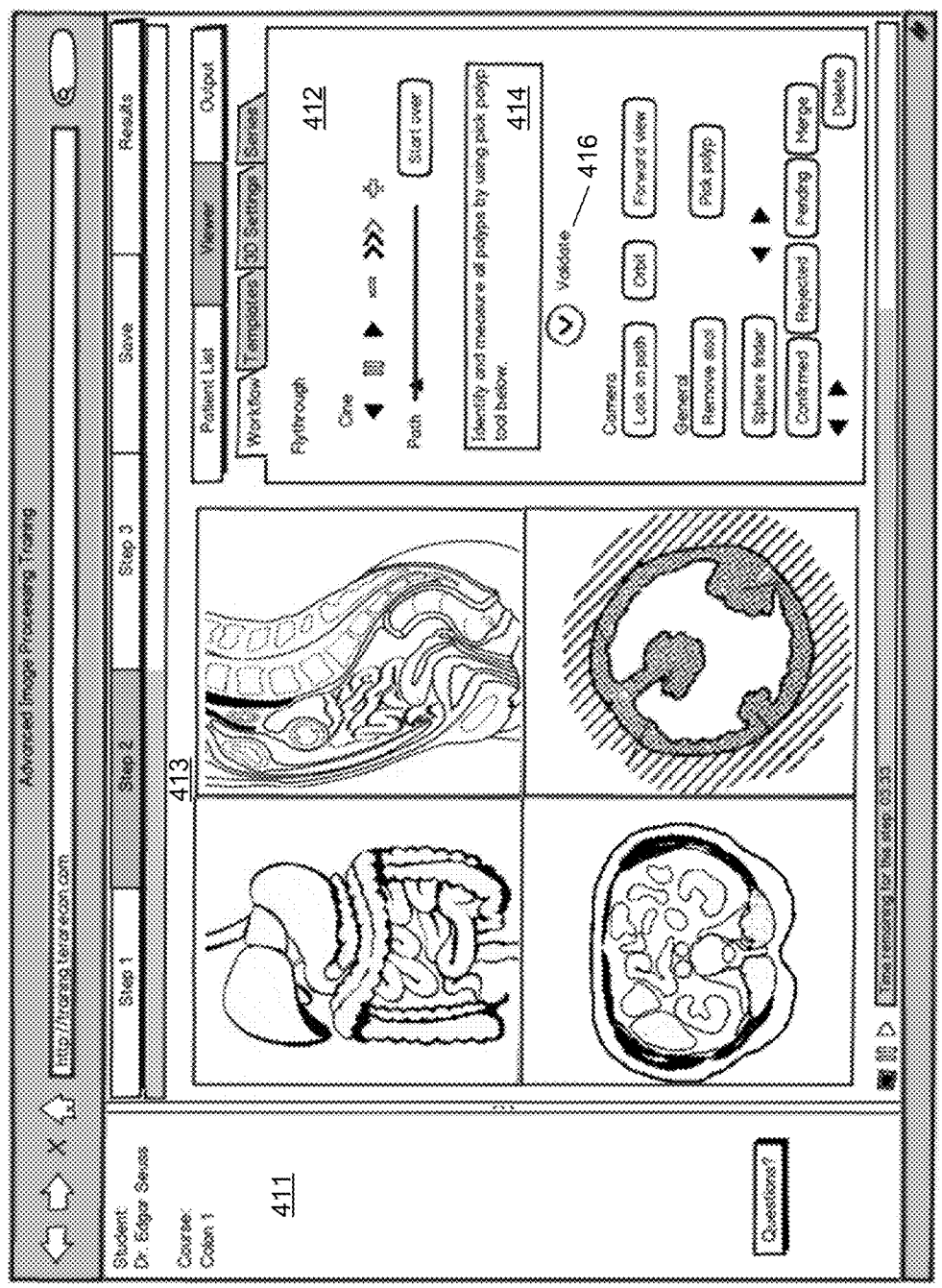
Figure 4E:
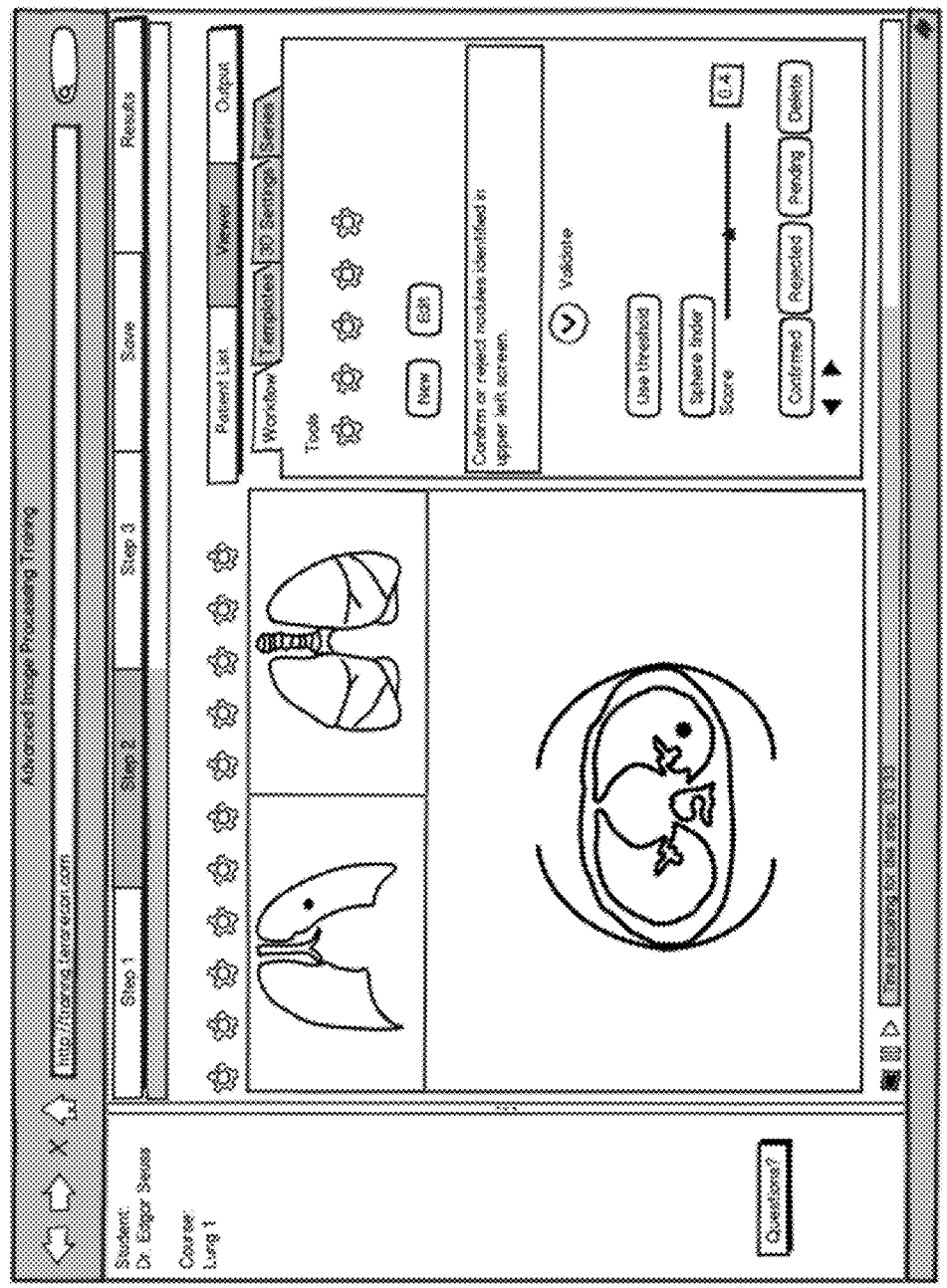
Figure 4F:
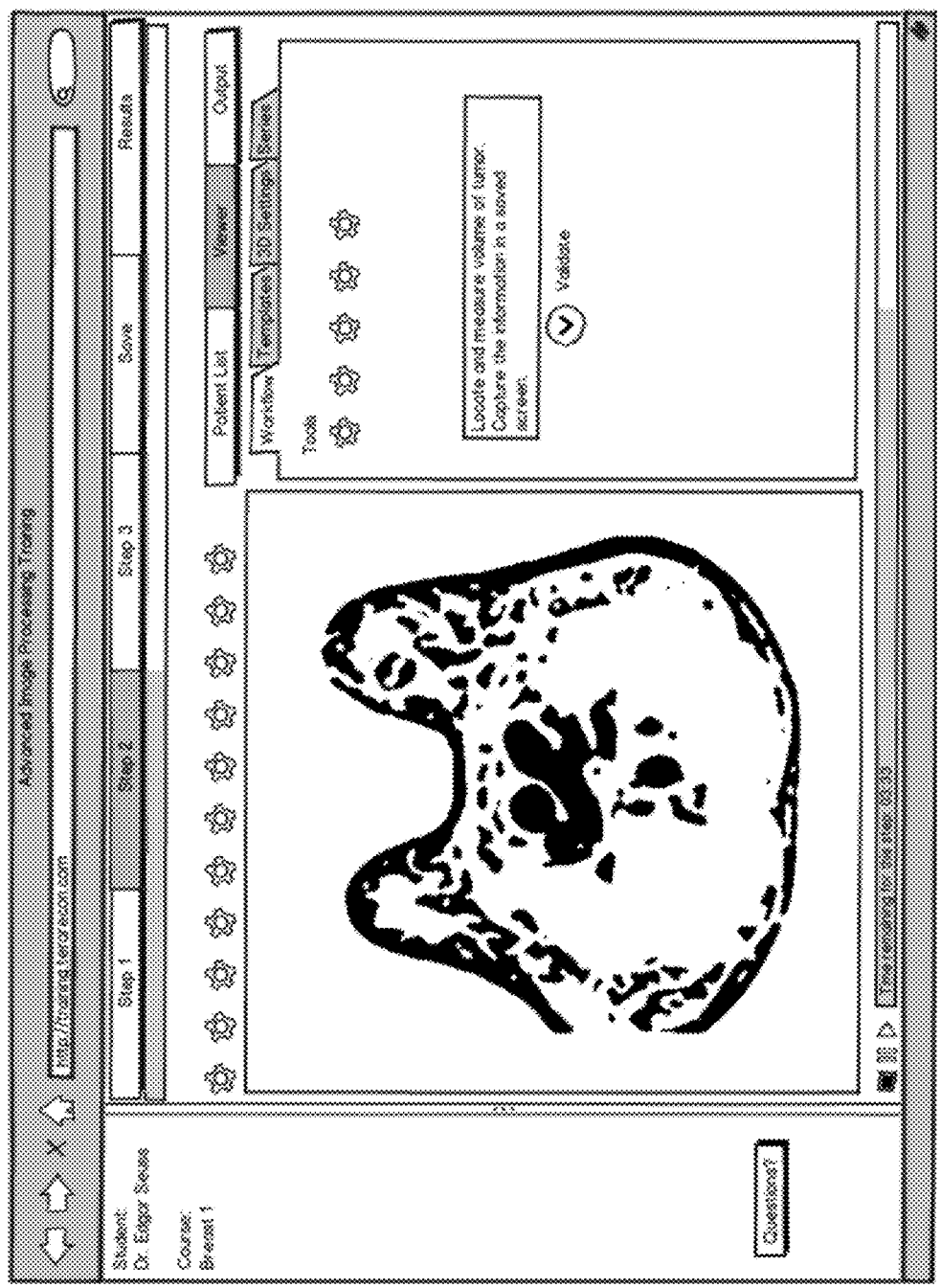
Figure 4G:
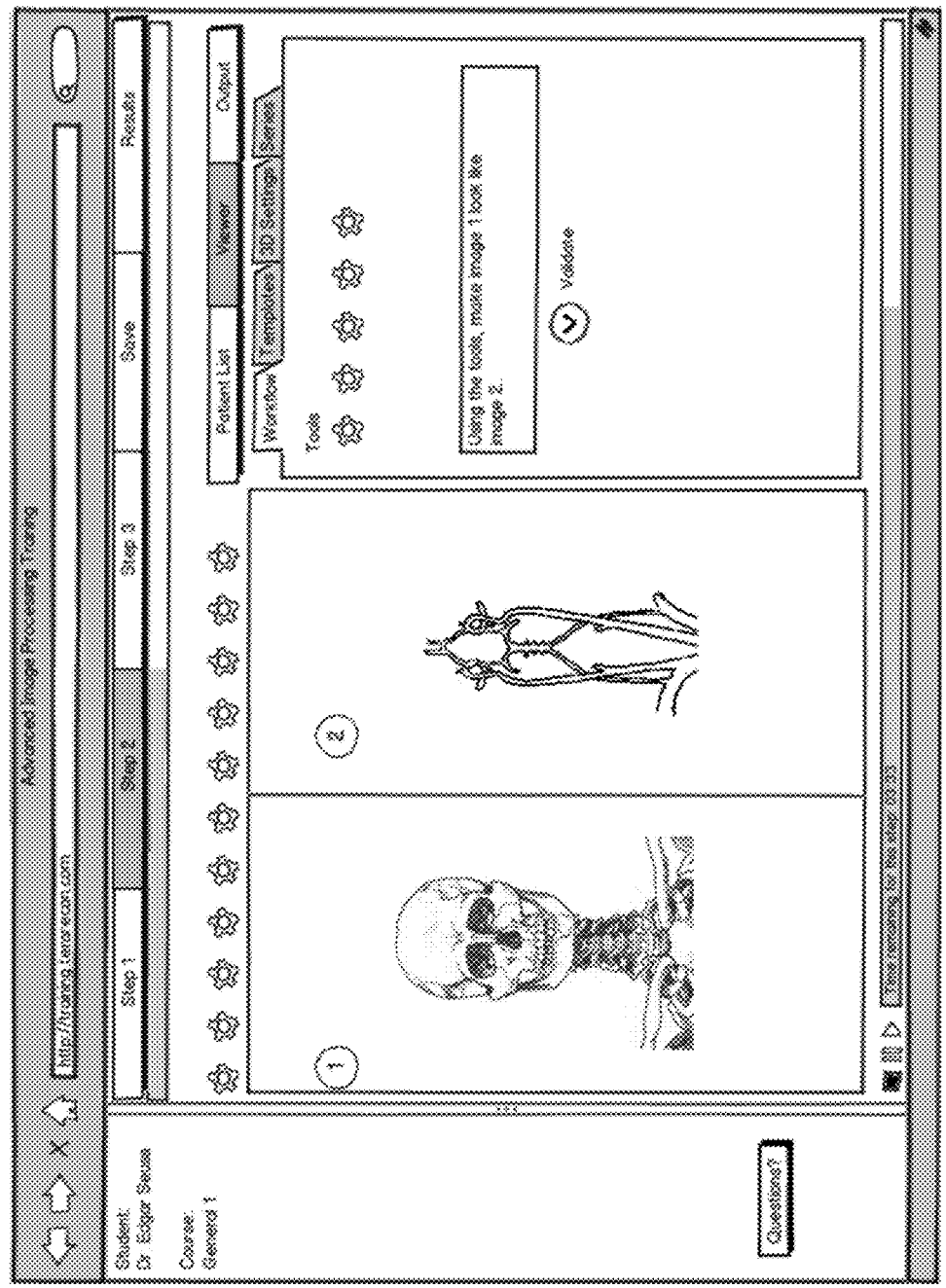
Figure 4H:
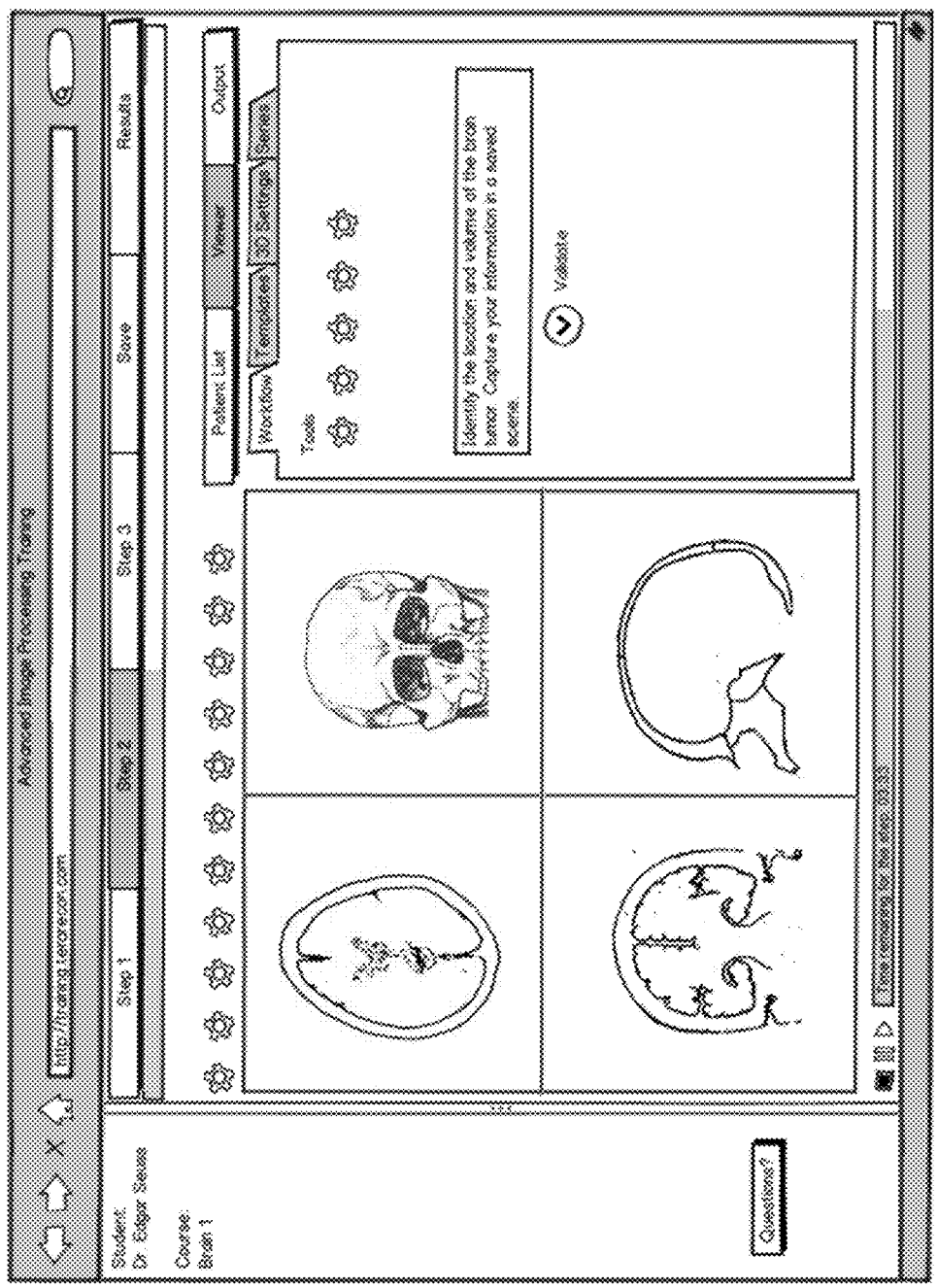

FIGS. 4D-4H are screenshots illustrating some other examples of training courses. For example, a colon course is shown in FIG. 4D. An instructor can ask via instruction box 414 a student to identify and measure a body part of a medical image currently displayed using some of the tools represented by icons that are available to that particular image and/or course. Alternatively, a lung course is shown in FIG. 4E. A student may be prompted to confirm or reject certain elements of an image currently displayed, such as nodules or polyps. Further shown in FIG. 4F is a breast course. An instructor may prompt a student to locate and measure a certain element within an image currently displayed. An instructor may also request a student to produce an image rendering (as shown in FIG. 4G), which may transmit an image rendering command to be processed by the imaging processor server. The student may also be able to ask the instructor or other students' questions during the course, either by email, chat, voice-over-IP or other ways. FIG. 4H shows an example of a brain course.

In one embodiment, when the student has completed the course, he may be able to see his results immediately if the scoring/grading is done automatically, at least in part. Or he may submit his results and need to wait for his instructor to evaluate all or part of his course results. The student may get a notice by email or other means when his results are ready. When the student sees his results, he may see the results for the entire course, each step within the course, or a combination of both. He may also see his score, relative to, or ranking within other students who have taken the course. This contextual presentation may include current students', and/or historical students' scores.

Figure 4I:
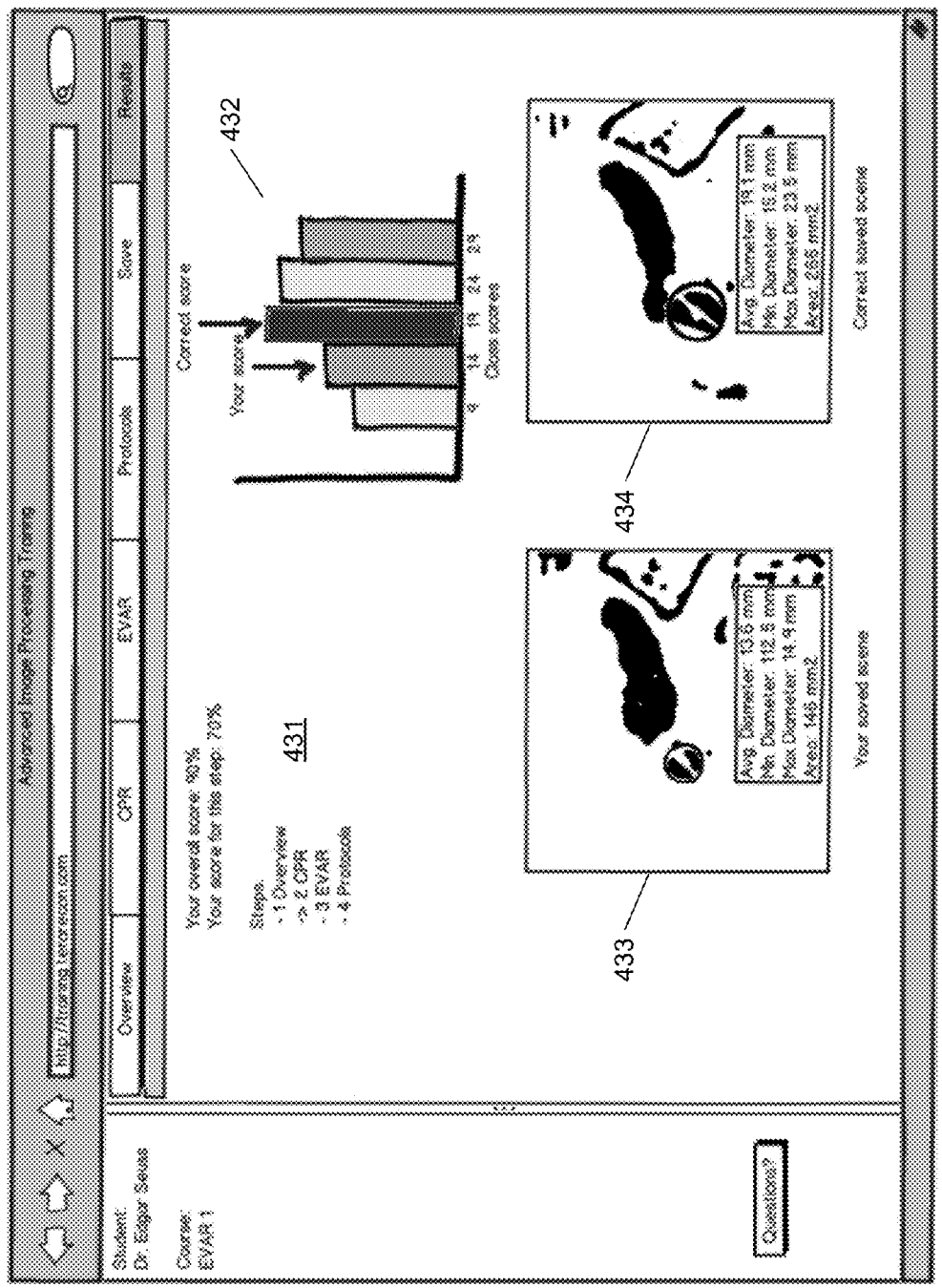

When viewing his results, a student may see his screenshots, or scenes, next to those of the instructor. The differences between the scenes may be highlighted. The student may be offered the option of taking the course again. This option may be controlled by the instructor, either on a course basis, or on an individual student basis. Once a course is completed satisfactorily, it may be stored in the system as completed so that courses relying on it as a prerequisite are triggered to now be available to the student in his course listing. FIG. 4I shows an example screen of a student's results. This screen shows the student's overall score and step score 431. In addition there is information on one of the steps of the course, in this case, the CPR step of an EVAR 1 course. A graph, 432, is shown which compares the student's score to those of the class. Also, the student can see a screenshot of his answer, 433, next to a screenshot of the instructor's correct answer, 434.

Figure 5A:
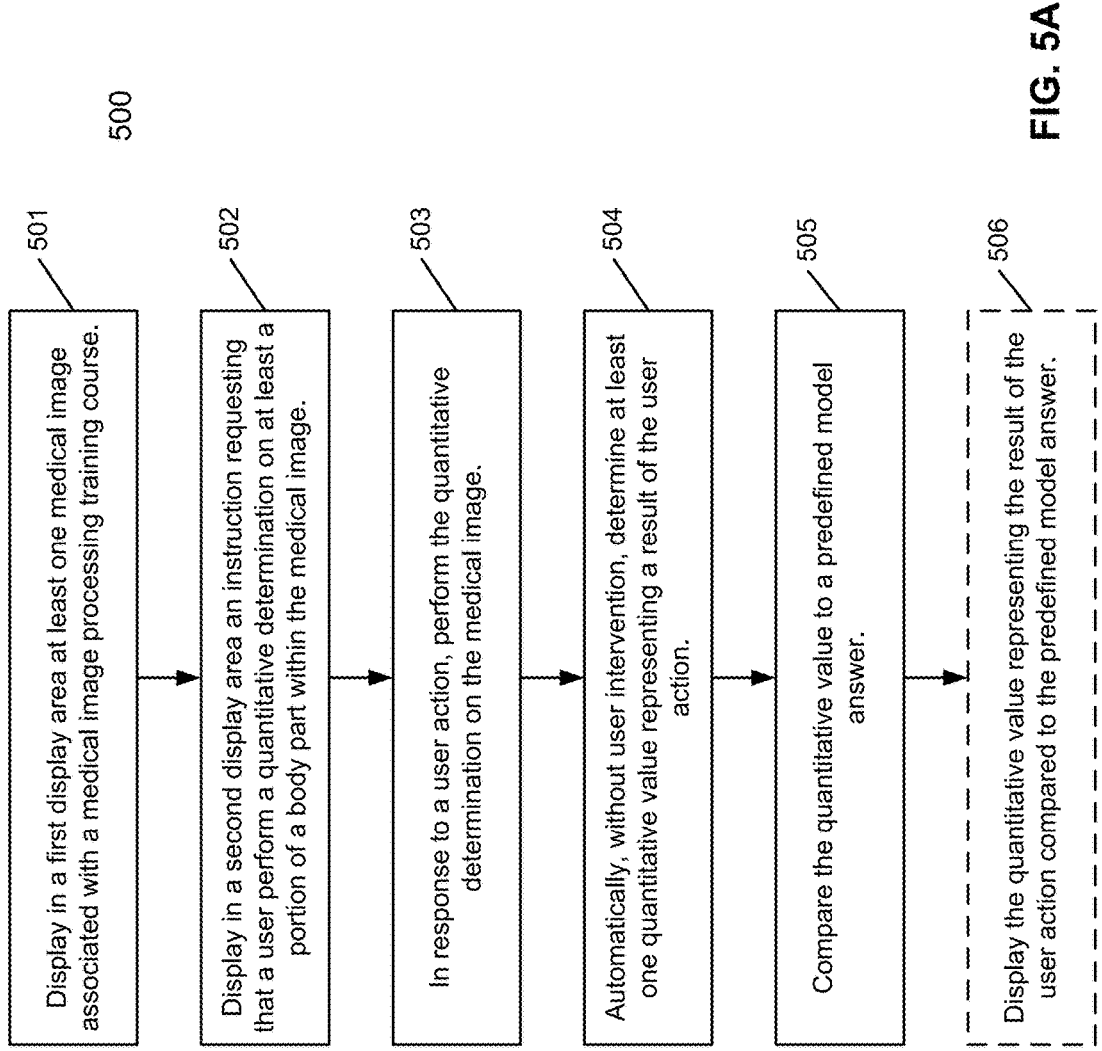
FIG. 5A is a flow diagram illustrating a method for providing medical image processing training according to another embodiment of the invention.

FIG. 5A is a flow diagram illustrating a method for providing medical image processing training according to another embodiment of the invention. Method 500 may be performed by medical image processing training system 107 of FIGS. 1-2, which may include software, hardware, or a combination thereof. Referring to FIG. 5A, at block 501, processing logic displays at least one medical image associated with a medical image processing training course. A training course may instruct a user to perform certain image processing using at least one tool available from an image processing server. Alternatively, a training course may request a user to perform a quantitative measurement of, or locate, or identify, a body part within a medical image. Alternatively a training course may request an answer to a question. At block 502, processing logic displays an instruction to the user requesting that the user perform some sort of quantitative determination on at least one body part within the medical image. The quantitative determination may be a measurement. The measurement may be a 2-dimensional measurement or a 3-dimensional measurement. The measurement may be a distance, an area, a volume, an angle or any other type of measurement. The body part may be an entire body part, such as a heart, or a lung, or may be a partial body part, such as a portion of a blood vessel or a portion of the digestive tract. The body part may be morphological, or inherent, such as a kidney, or pathological, or disease related, such as a polyp or a nodule.

In response to a user action, at block 503, displayed quantitative determination is performed on the medical image. At block 504, processing logic determines at least one quantitative value representing a result of the user action. For example, if the user performed a measurement of the diameter of an artery at a specified location, the quantitative value would be the actual diameter measurement, for example, 4 mm. At block 505, processing logic may automatically calculate a score for the quantitative determination in view of a predefined model answer associated with the question by comparing the value representing the result of the quantitative determination to the predefined model answer. The score may be calculated at the end of the course or offline. At block 506, optionally, processing logic displays the score and/or the statistics concerning user performance of the training course.

Figure 5B:
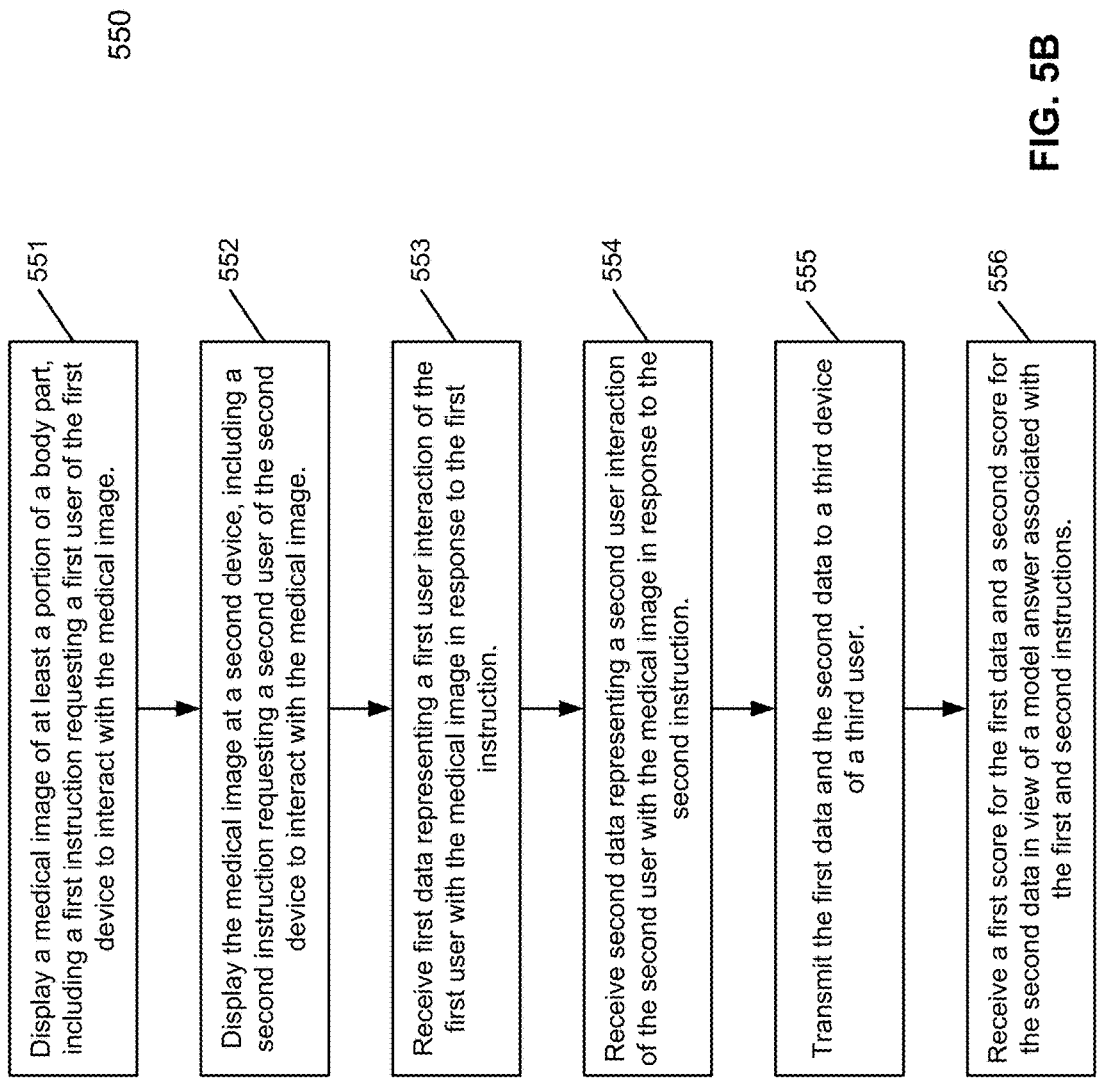
FIG. 5B is a flow diagram illustrating a method for providing medical image processing training according to another embodiment of the invention.

FIG. 5B is a flow diagram illustrating a method for providing medical image processing training according to another embodiment of the invention. Method 550 may be performed by medical image processing training system 107 of FIGS. 1-2, which may include software, hardware, or a combination thereof. Referring to FIG. 5B, at block 551, processing logic displays a medical image of at least a portion of a body part, including a first instruction requesting a first user of the first device to interact with the medical image. At block 552, the medical image is displayed at a second device, including a second instruction requesting a second user of the second device to interact with the medical image. At block 553, processing logic receives first data representing a first user interaction of the first user with the medical image in response to the first instruction. At block 554, processing logic receives second data representing a second user interaction of the second user with the medical image in response to the second instruction. At block 555, the first data and the second data are transmitted to a third device of a third user. At block 556, processing logic receives a first score for the first data and a second score for the second data in view of a model answer associated with the first and second instructions.

Figure 6A:
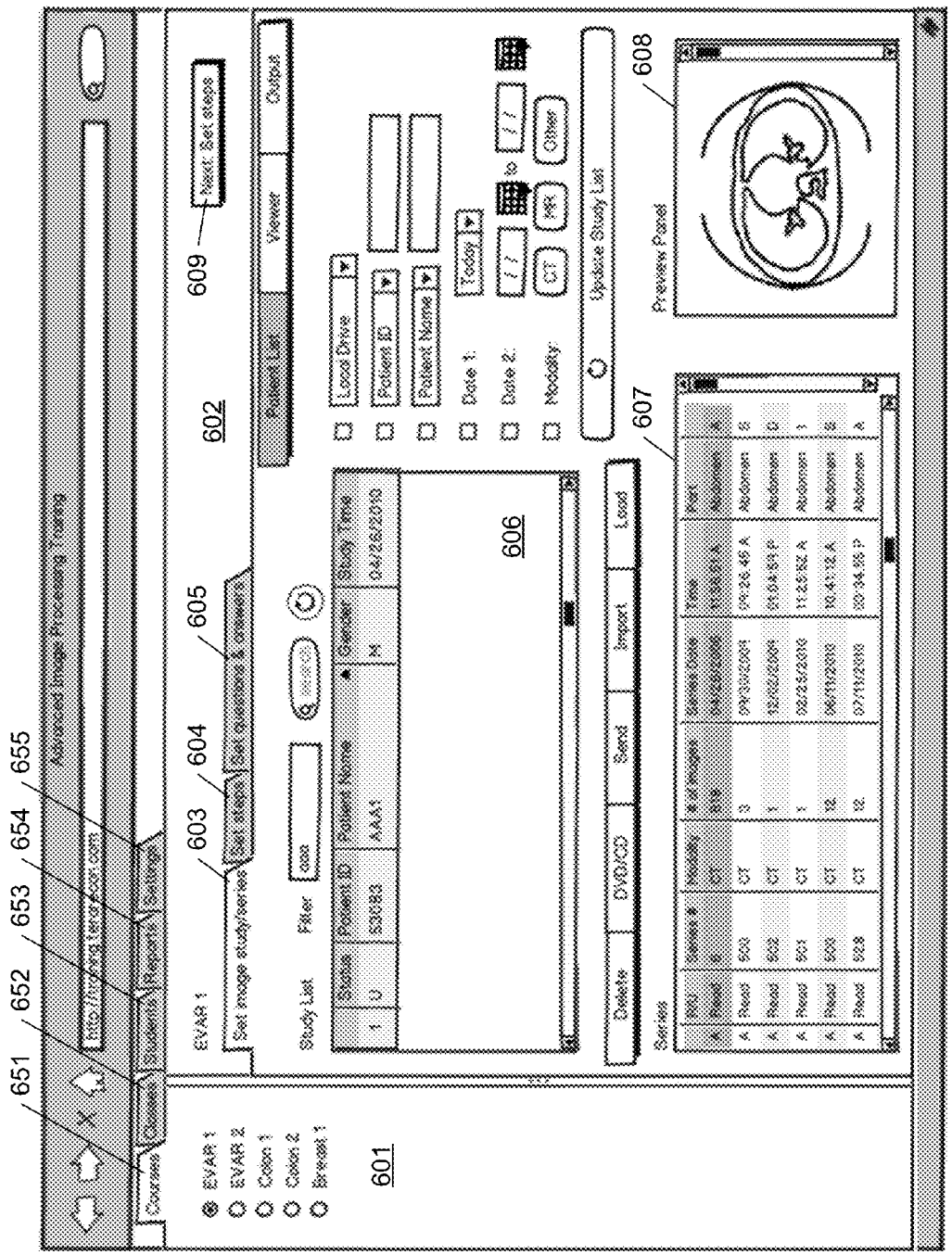
FIGS. 6A-6E are screenshots illustrating a graphical user interface for providing a medical image processing training course according to certain embodiments of the invention.

FIGS. 6A-6E are screenshots illustrating a graphical user interface for creating a medical image processing training course according to certain embodiments of the invention. FIGS. 6A-6E may be presented by training system 107 of FIG. 1. An instructor may log into the system with a username and password. After logging in, the instructor may be shown a screen which includes the courses that he teaches, as shown in FIG. 6A. Instructors may be qualified to teach particular courses and not others. In general, he will only have access to the courses that he is qualified to teach. Each course may need to be set up with the appropriate study, image series, steps, questions, potential answers, correct answers, comments, answer ranges, etc. so that the course can be properly displayed and graded/scored/evaluated.

FIG. 6A shows a possible screen showing how an instructor may begin to set up a new course by identifying a study and study series as the basis for a course. The GUI as shown in FIG. 6A includes multiple tabs 651-655 representing different options available to the user. In this example, course page 651 is selected. The courses available to this instructor are listed in display area 601. In this example, the course, EVAR 1, has been selected and detailed information of the selected course is displayed in display area 602. In this embodiment, there are multiple tabs 603-605 representing the steps or stages for configuring the selected course. A listing of the available studies 606 is displayed. In addition, a list of study series 607 associated with a study selected from study list 606 is displayed, and one or more images associated with a study series selected from list 607 is displayed via preview panel 608.

The instructor can search or browse through the studies to locate the one he wants. In this example, the instructor has searched using the search term "aaa" and found a study with patient name "AAA1" and has selected this study. Within this study, several study series are available. The instructor has chosen study series #6 in this example. Once the instructor has selected the study and series for the course, he pushes the next button 609. He may be prompted to designate a workflow with which the series should be loaded. For example, he may select an "EVAR" workflow or a "volume browse" workflow. Alternatively the software may automatically select the workflow for the instructor.

Figure 6B:
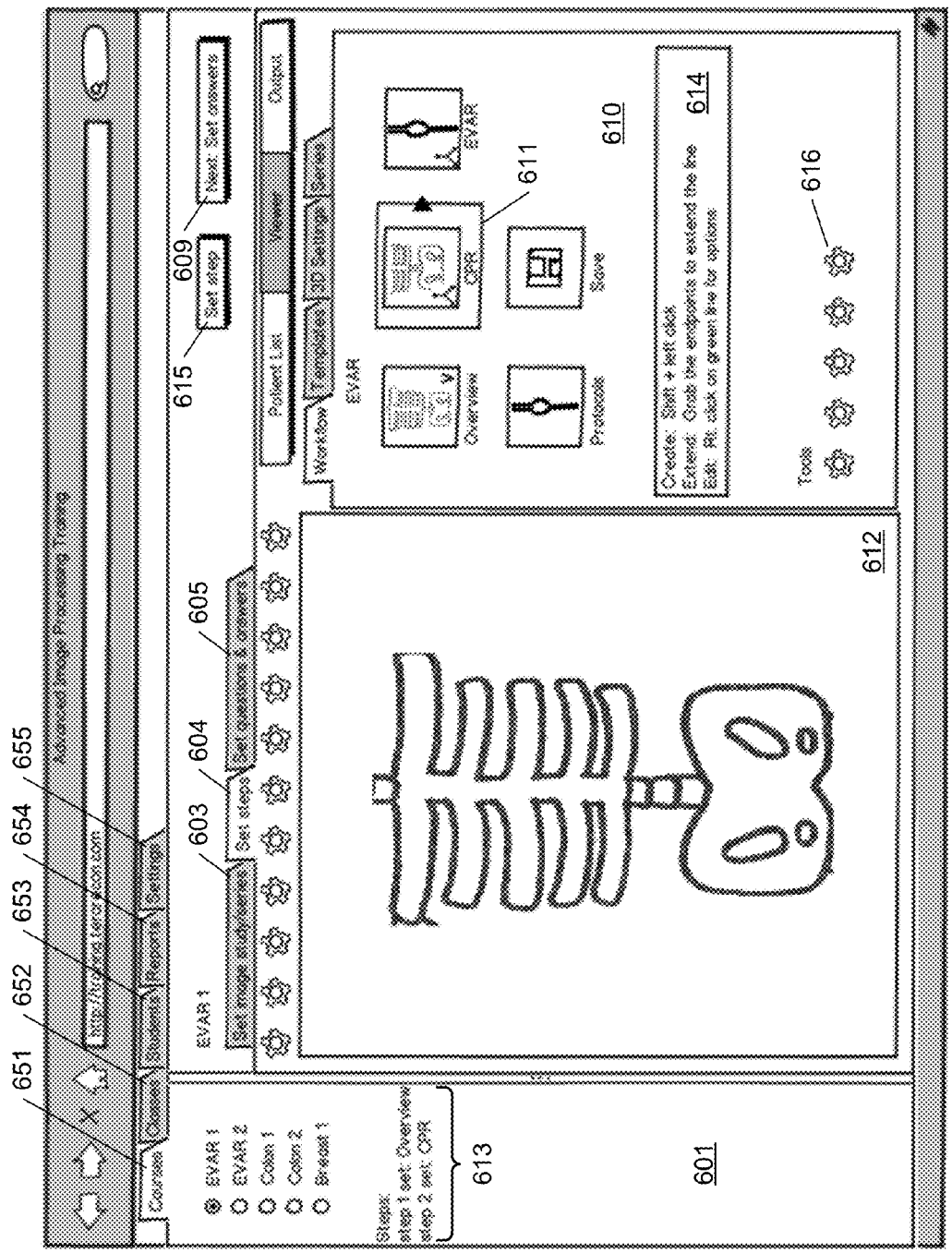

FIG. 6B shows a possible screen showing how an instructor may set the steps for a particular course. The GUI as shown in FIG. 6B may be presented as part of tab 604 in response to button 609 of FIG. 6A (tab 603). In this example, there are predefined workflow stages or steps of a workflow, associated with the selected study series, displayed in display area 610 which the instructor may select. The workflow stages are presented by graphical representations such as thumbnail images or icon, and each of them is selectable. In response to a selection of one of the graphical representation, in this example, workflow stage 611, an image, or images, is displayed in display area 612. The instructor may also create his own steps rather than following a predetermined workflow. In this example, the instructor has already validated step number 1: Overview, and is now working on step number 2: CPR. Note the step listing 613 is displayed in display area 601, which lists the steps as they have been added to the course. The instructor can also add instructional text in instruction box or field 614 to help the student with the step. In addition, a set of graphical representations 616 representing a set of tools is displayed to allow the instructor to associate or specify the tools to be used by the students. The instructor may validate the step using a validate or set-step button 615, before moving on to the next step. When the instructor is done creating steps, he may push a next button 609 to progress to the next task.

Figure 6C:
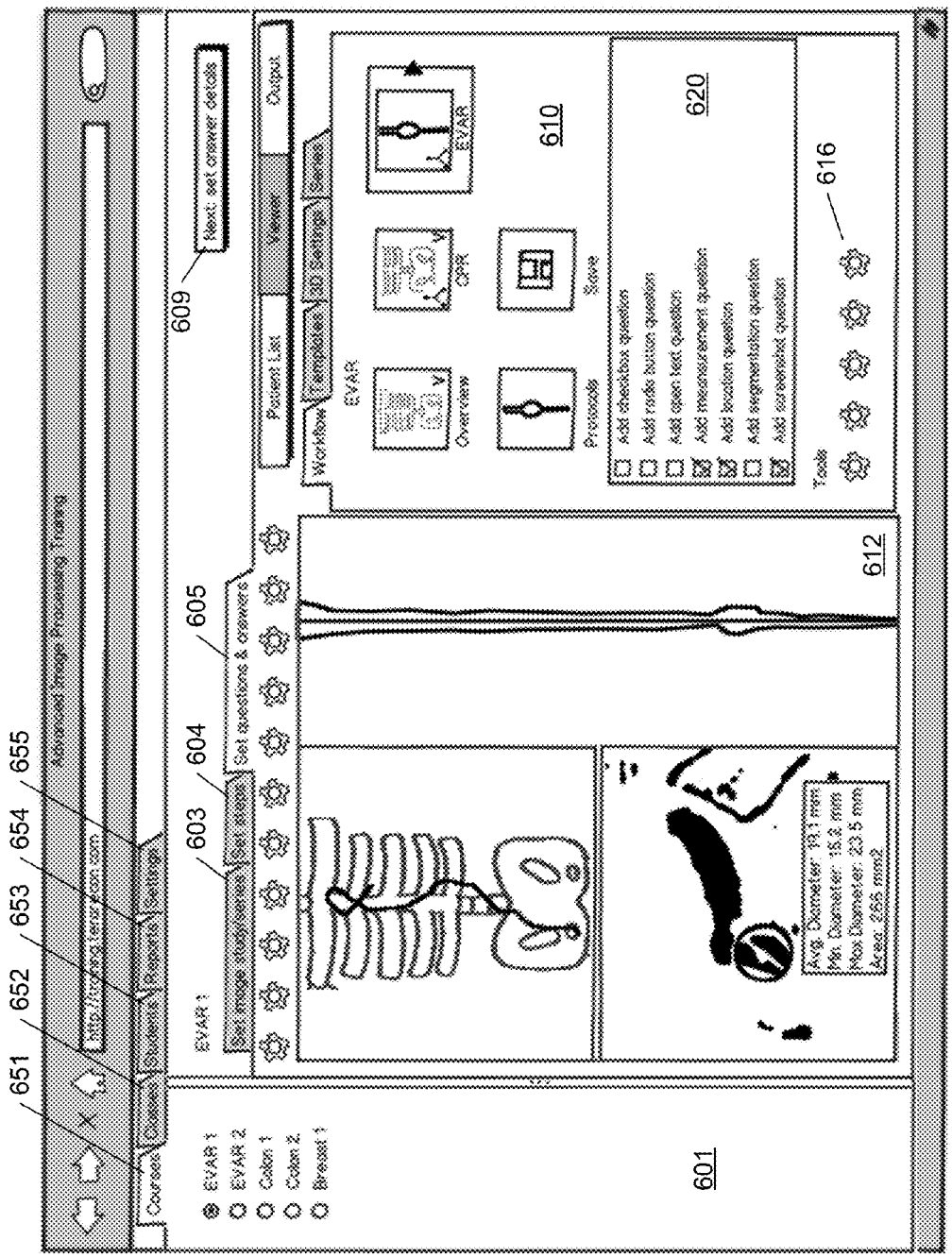

FIG. 6C shows a possible screen showing how an instructor may set the questions and correct answers and ranges for a step, or question, of the course. Different types of questions are available to the instructor and are listed in the question type list 620. Other question types may be available. The instructor may choose more than one question type. In this example, the instructor has chosen 3 different question types for this step in the course. Question types 620 may include a variety of different types of questions. For example, a question can be a checkbox question, which is a multiple choice question where multiple selections are possible. This type of question can be scored automatically. A question can be a radio button question, which is a multiple choice question where only one selection is allowed. This type of question can be scored automatically. A question can also be an open text question, which is a question where the response is open, freeform text. This type of question can generally not be scored automatically, although some key word searching algorithms can be used.

In one embodiment, a question may be a measurement question, which asks a user to capture a measurement on a screen and/or the quantitative value associated with the measurement. The measurement may be a length, area, volume, angle or other type. Several different units of measurement may be used including mm, degrees, $mm^2$, $mm^3$ etc. The quantitative aspect of this type of question can generally be stored and scored automatically. The screenshot of the measurement may need to be scored by the instructor.

The quantitative component of this type of questions can be compared automatically to that of the answer where the advanced imaging software captures the quantitative info. For example, if the question in the test asks for the student to identify and measure the diameter (or volume, etc.) of a polyp, the student may use his mouse or cursor or a pointer to identify the location of a polyp. He or she may then use the tools to determine the diameter (or other parameter) of the polyp. In one embodiment, this quantitative data (the diameter etc.) is stored in such a way that the information can be automatically compared to the answer the instructor has provided as a correct answer. If the instructor has provided a range for the correct answer, the training software can also determine whether the student's quantitative answer is within the acceptable measurement range.

The storage of the quantitative data may be in a database, XML or other standard. The storage may be long term, or only long enough to interact with the training software. The data may be stored in the training software, the advanced imaging software, or both. When the instructor sets ranges for a quantitative answer, he/she may set them manually, as shown in FIG. 6E, or the training software system may provide defaults. There may be one default (such as within 10%), or there may be several defaults, such as "tight", "medium" or "loose". The instructor may choose a tight range for an advanced class, but a looser range for a beginner class. The default ranges may be a percentage of the measurement or may be based on some other parameter, or may be absolute.

A question may also be a location question, which asks a user to capture a location on the screen. The advanced image processing software will generally capture the x, y, and z coordinates which can then be evaluated automatically. Similar to the measurement type of question above, the quantitative measurements for this type of question can be stored, compared, and have ranges applied.

A question may also be a segmentation question, which may prompt a user to, for example, isolate a volume of anatomy to better view and evaluate it. The anatomy might be bone, an organ, blood vessel, colon, tumor, nodules, polyps, etc. This type of question may be able to be scored automatically since the advanced image processing software may capture the location and measurement coordinates. A screenshot may also accompany this type of question for manual evaluation. Note that segmentations can be done in 1 dimension, 2 dimensions or 3 dimensions. The dimension of time can also be brought in as a factor. For example, a question could be "segment the right ventricle during peak systole." To answer this question, a student would need to be able to identify systole, where the ventricle is during systole, and the outline of the ventricle during systole.

This question type is more complex than either the location or measurement type question in that it involves multiple locations and possibly measurements. However, similar to the measurement type of question above, the quantitative measurements for this type of question can be stored, compared, and have ranges applied. For example, the ranges could be applied to any part of the segmentation (no point of the segmentation can be more than 10% from the instructor's location, for example), or the ranges can be applied to the average or in other ways. For example, if average were used, the instructor might determine that the location may not be more than 10% from his identified location on average. So if one point is 12% off and one is 7% off, the average of these two points would be less than 10%. This concept could be applied over a large volume of points.

A question may also be a screenshot question, which asks for a student to take a screenshot, or save a scene during the processing of an image. This type of question can generally not be scored automatically, although some location and measurement data may be automatically pulled from the screenshot.

Referring back to FIG. 6C, when the instructor is finished identifying the question types for a given step, he may click on a next button 609 to progress to the next task.

Figure 6D:
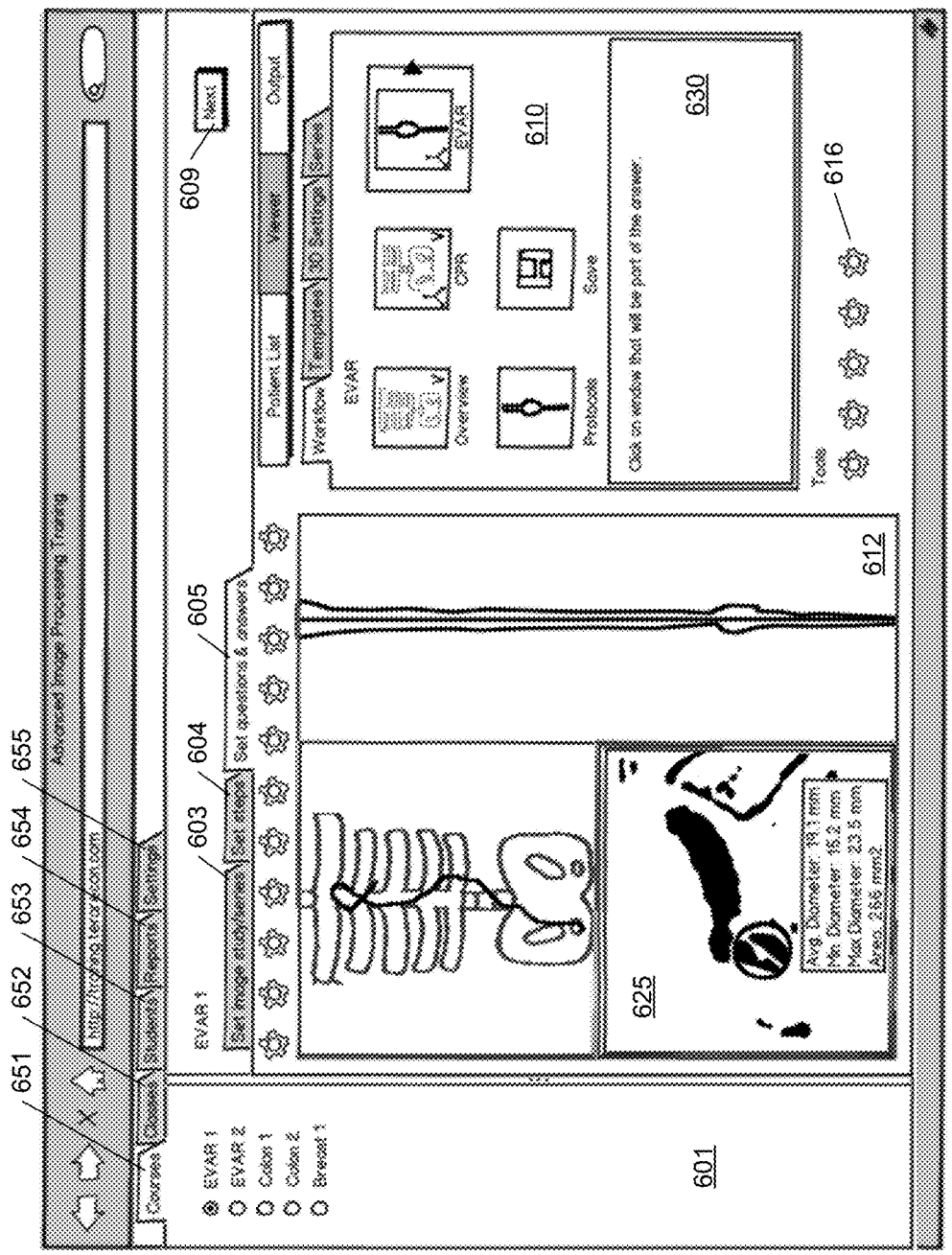
Figure 6E:
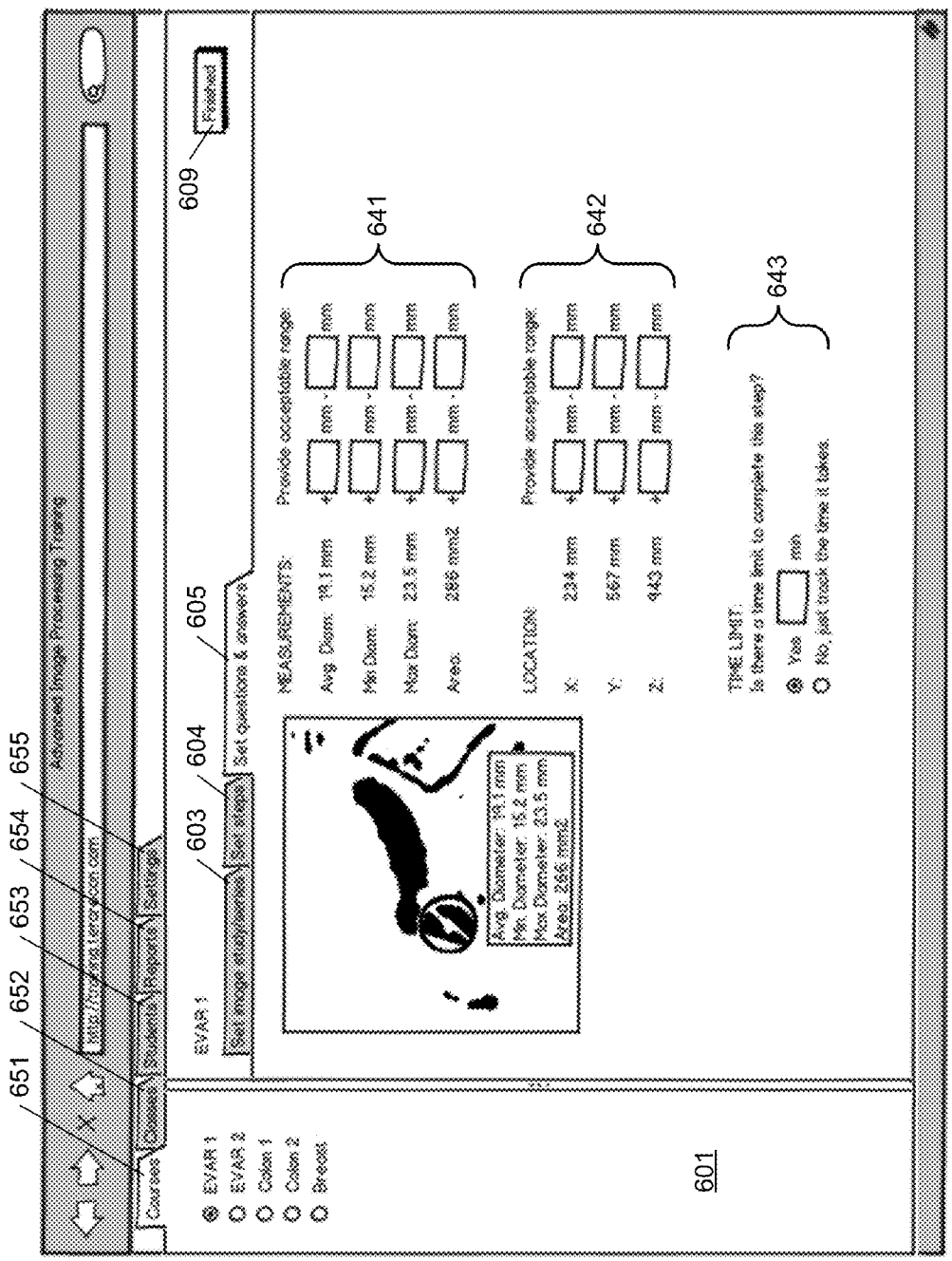

FIG. 6D shows a possible screen showing how an instructor may set the specific information for a given step of a course. The GUI as shown in FIG. 6D may be presented in response to an activation of button 609 of FIG. 6C. In this example, the instructor selects an image for a screenshot type question. Instructions for the question type are included in the instruction box 630. In this example the instructor is asked to select a screen. The instructor selects the lower left screen 625, and then clicks next button 609 to proceed to the next question. This process can be iteratively performed for each of the questions to be provided.

FIG. 6E shows another possible screen showing how an instructor may set the specific information for a given step of a course. In this example, the instructor is shown the screenshot he has selected in the previous step in FIG. 6D. He is also asked to provide detail relating to the other 2 question types he has identified with respect to this step in the course, a measurement question and a location question. In this example, the measurement and the location of the measurement have already been preset by the instructor in the set steps process and the results are shown here. The instructor is asked to include ranges in range text boxes 641-642 for both the location and measurement of the anatomy. These ranged define how close to the instructor's solution the student needs to come to get the question correct. The instructor may also set a time limit 643 for this step, or may track the time each student takes to complete the step. When the instructor has completed this task, he may push the next button 609 to move on to the next step or task. Some question types, such as the open text question, may require manual grading/scoring by the instructor.

Figure 7:
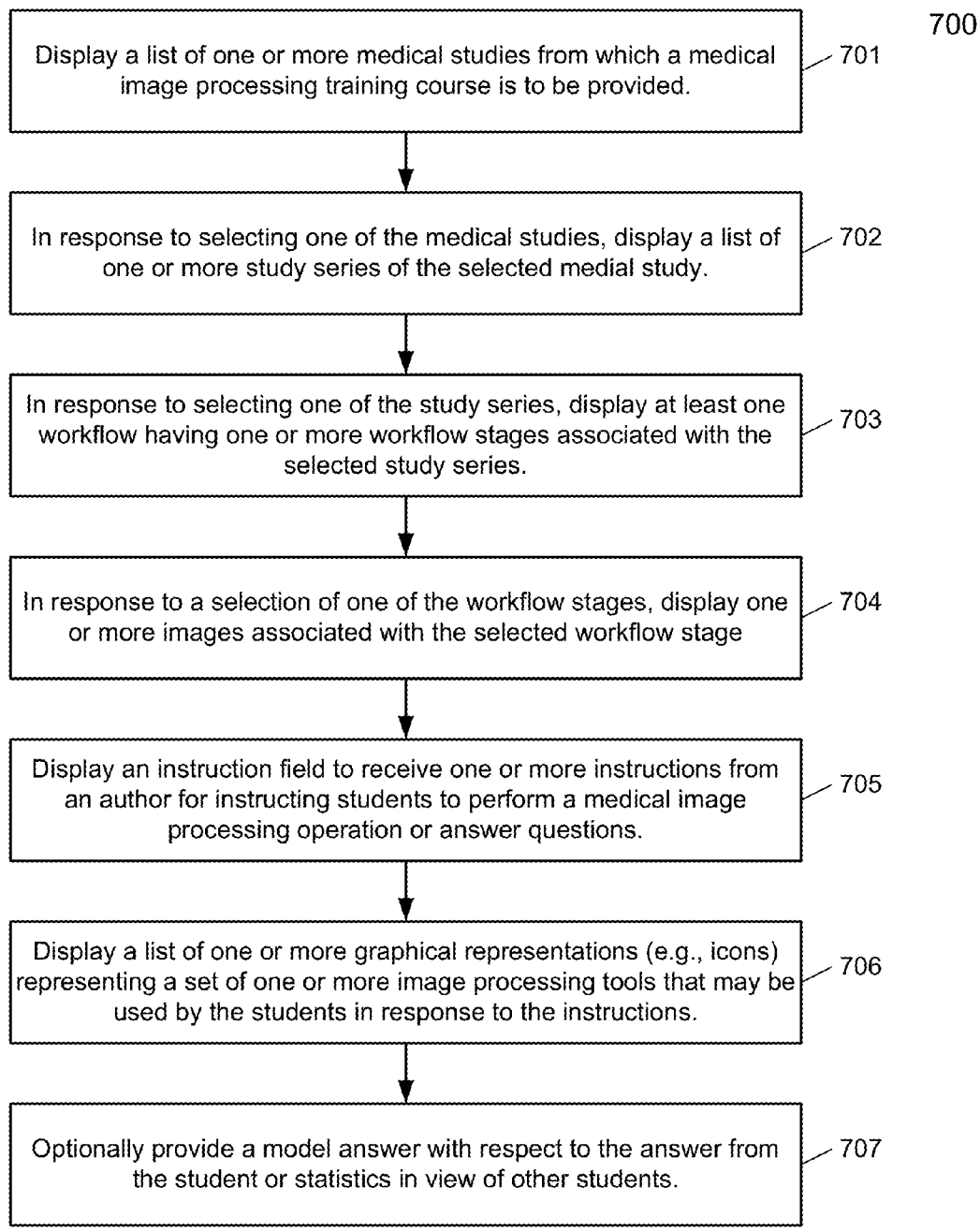
FIG. 7 is a flow diagram illustrating a method for providing an image processing training course according to one embodiment of the invention.

FIG. 7 is a flow diagram illustrating a method for providing an image processing training course according to one embodiment of the invention. Method 700 may be performed by course configuring module 110 of FIG. 1. Referring to FIG. 7, at block 701, processing logic displays in a first display area a list of one or more medical studies from which a medical image processing training course is to be provided. In response to a selection of one of the medical studies, at block 702, a list of one or more study series associated with the selected medical study is displayed in a second display area. At block 703, in response to a selection of one of the study series, processing logic displays at least one workflow associated with the selected study series in a third display area, including one or more graphical representations representing one or more workflow stages or steps of the workflow. In response to a selection of one of the workflow stages, at block 704, one or more images associated with the selected workflow stage are displayed in a fourth display area. At block 705, processing logic displays an instruction box or field in a fifth display area to receive one or more instructions from an author for instructing students to perform a medical image processing operation. The instructions can include one or more questions in one or more of the question types described above. At block 706, a list of one or more graphical representations (e.g., icons) is displayed in a sixth display area representing one or more image processing tools that may be utilized in response to the instructions provided by an instructor. At block 707, a model answer or statistics with respect to an answer or image processing result from the student (or in view of other users) is optionally displayed.

Figure 8A:
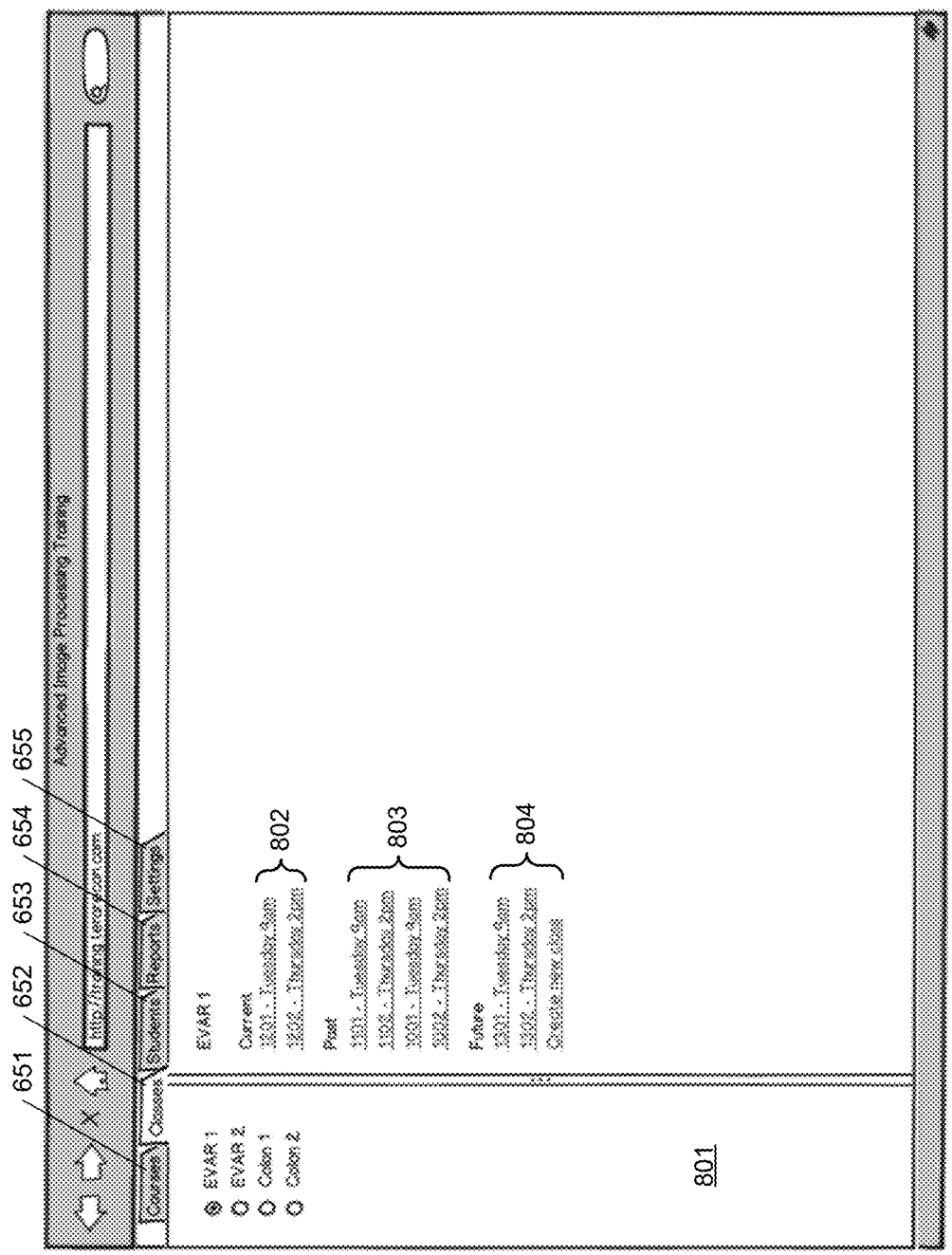
FIGS. 8A-8D are screenshots illustrating a graphical user interface for a medical image processing training course according to certain embodiments of the invention.

According to one embodiment, a class is made up of a group of students. Each course may have multiple classes. For example an instructor may at any time be teaching more than one class per course which includes different students. For example, he may have a Tuesday Colon 1 class and a Thursday Colon 1 class. He may also have historical and future groups of students taking a course which will define past and future classes. FIG. 8A shows a possible initial class screen under tab 652. The courses are listed in a course listing 801. The class list for the selected course is also shown, including current classes 802, previous classes 803, and future classes 803. The instructor may drill down deeper within any given class to get more information. The instructor may also create new classes.

Figure 8B:
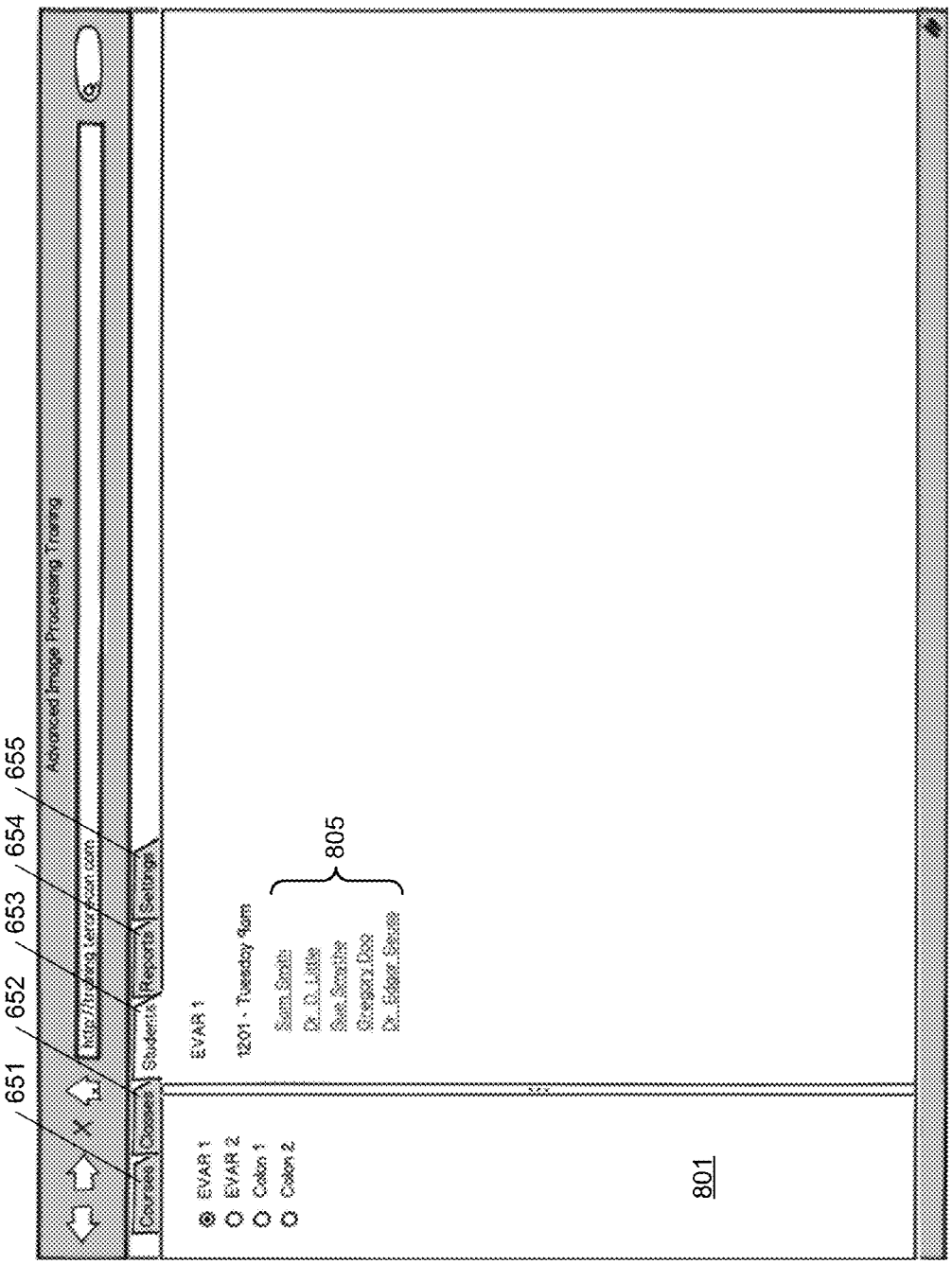

An instructor may want to look at students individually or in groups. He may want to look at all courses/classes taken by a particular or group of students. He may also want to control settings for individual or groups of students. FIG. 8B shows a possible initial students screen representing students under tab 653. The students for a selected course are listed in a student listing 805. More details, including test results and reports, for each student can be reached by clicking on a particular student link. Test results and report may include test scores, step scores, screen capture information, measurement and anatomy location information, timing information and other information related to the course.

Figure 8C:
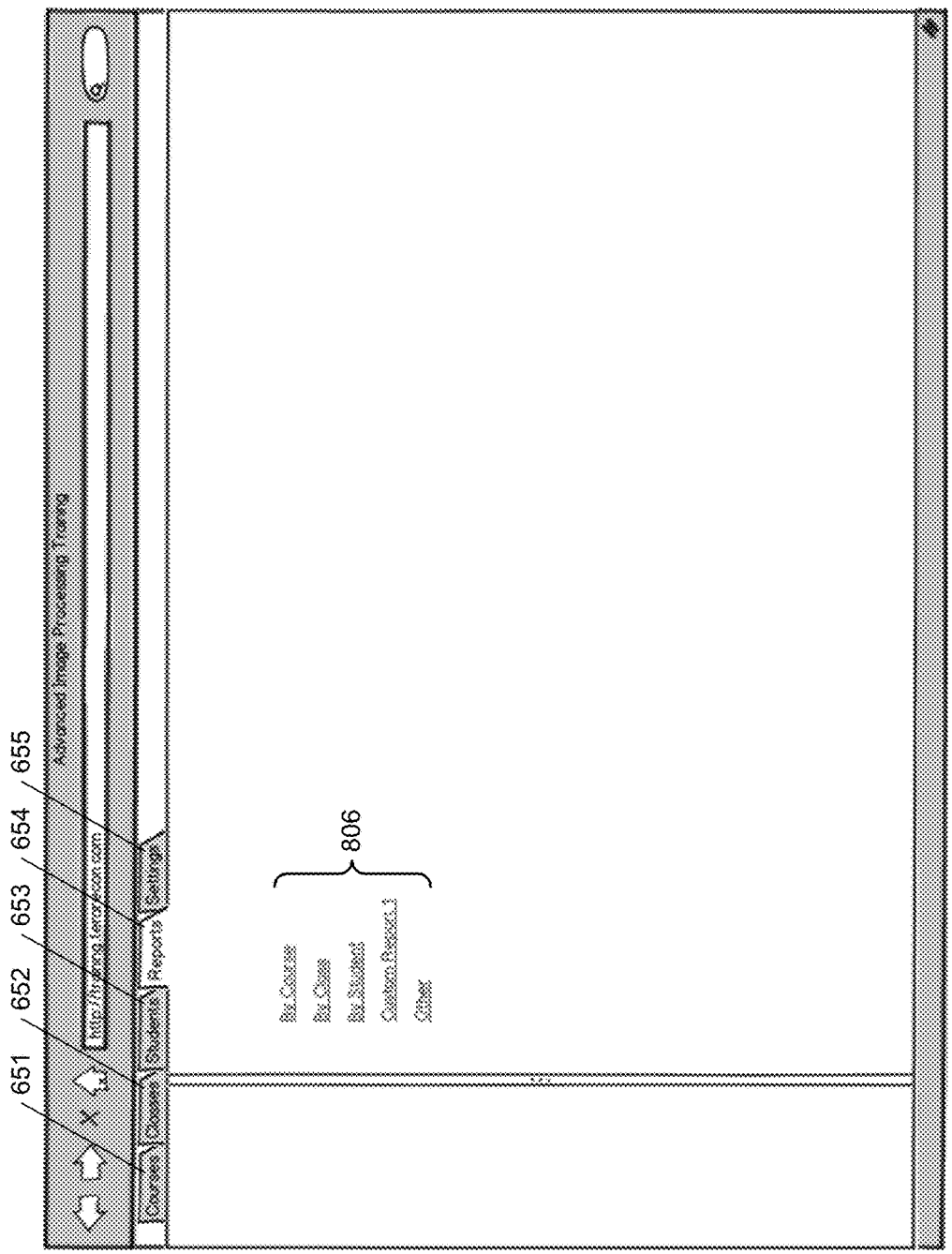

According to one embodiment, reports tab 654 may include reporting by course, by class, by student or other perspectives. For example, a report can be one student's grade in one course, or a summary of all students' results over time for all courses. An instructor may want to look at test completion times over the past few years, or even completion times at the step level, or an instructor may want to break down the data in other ways to create other reports. Report information may be presented in text format, numeric format, graphically, spreadsheet, database, or any other appropriate format. FIG. 8C shows a possible initial reports screen. Possible report types are listed here in a report listing 806. More details for each report type can be obtained by clicking on a particular report link.

Figure 8D:
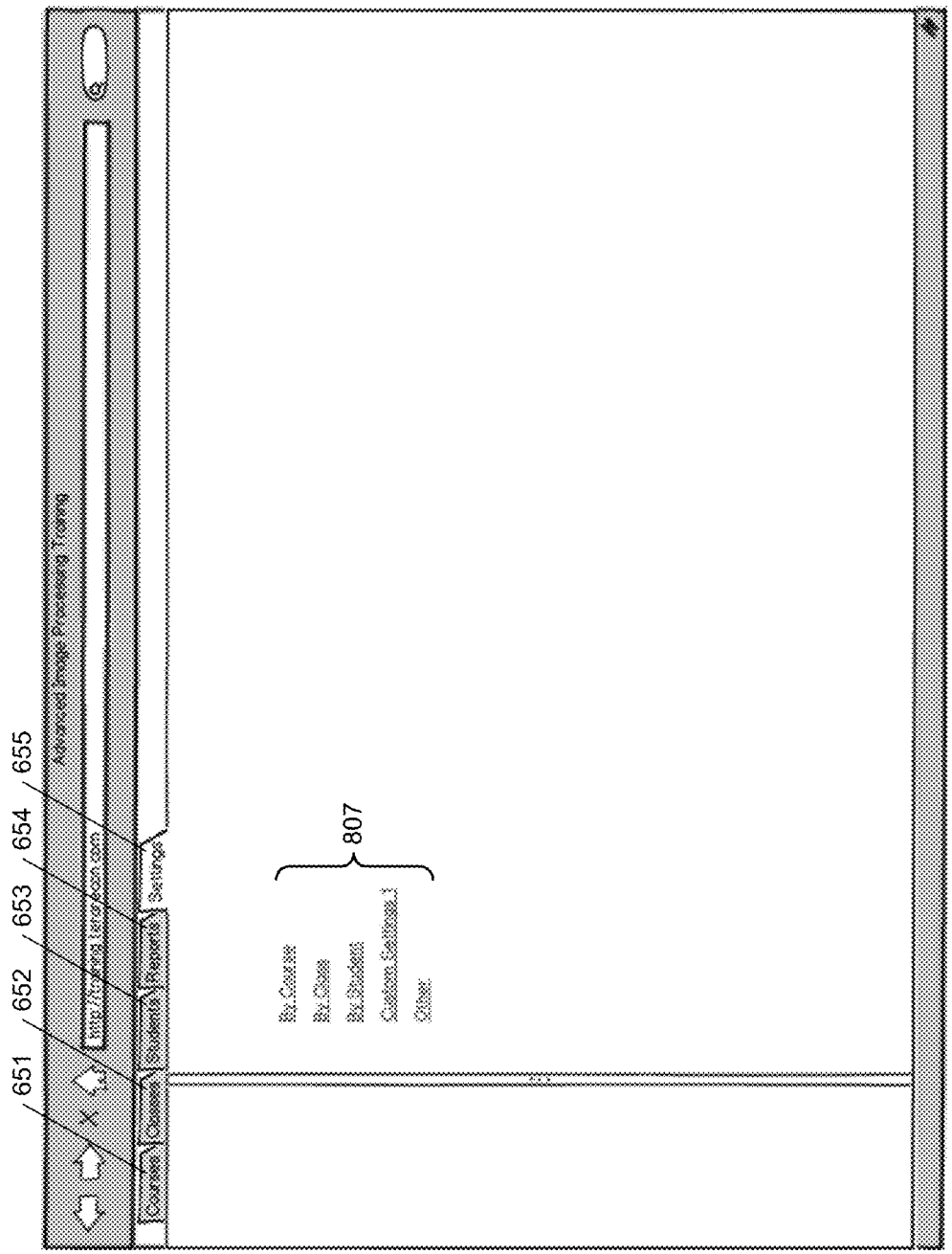

In one embodiment, classes and courses may have several configurable settings, such as time limits, answer ranges, whether or not students are allowed to retake steps or entire courses etc. FIG. 8D shows a possible initial settings screen under settings tab 655. Possible setting types are listed here in a setting listing 807. More details for each setting type can be obtained by clicking on a particular setting link.

Although the sample screens shown here are generally showing one clinical study/case per course, multiple clinical studies/cases per course are also envisioned. In this case, the course could be set up to step through the cases in a certain order, or to complete a certain number of cases, or complete a certain number of cases in a given time frame. Students may be able to choose which cases they complete for the course. For example, 10 cases may be required to complete the course, but there may be 12 cases available to choose from.

Also, a course may consist of only a portion of a workflow, so possibly only one step, or a few steps representing a stage or stages of a workflow. A course consists of at least one required step, but can contain many steps.

As mentioned earlier, the scoring, or grading of a course may be done automatically by the training software system, or manually, by the instructor, or a combination of the two. The results of the course can be broken down by student, by class, by course, by instructor, or combined in other ways. User access levels will determine how much of the results are visible. For example, a student may only be able to see his or her results, where an instructor may be able to see any of his results, for any course, class or student, but cannot see the results of other instructors unless he is given access. A university may choose to give instructors access to university-wide aggregated results for reference. In addition, a user, for example an instructor, may be able to give access to a third party, such as a parent, or another educational institution to which the student has applied.

Test results may also be used for certification purposes. In this situation, the certification process will likely define a minimum score for certification. This may be automatically determined or manually determined. Courses/classes can be offered either in a real time classroom format, or in a self-paced format. If a course is offered in a classroom setting, the scores for all the students can potentially be available during the classroom session. In this case, the instructor may have access to class screens where he can show anonymous results of the entire class to the class.

Figure 9:
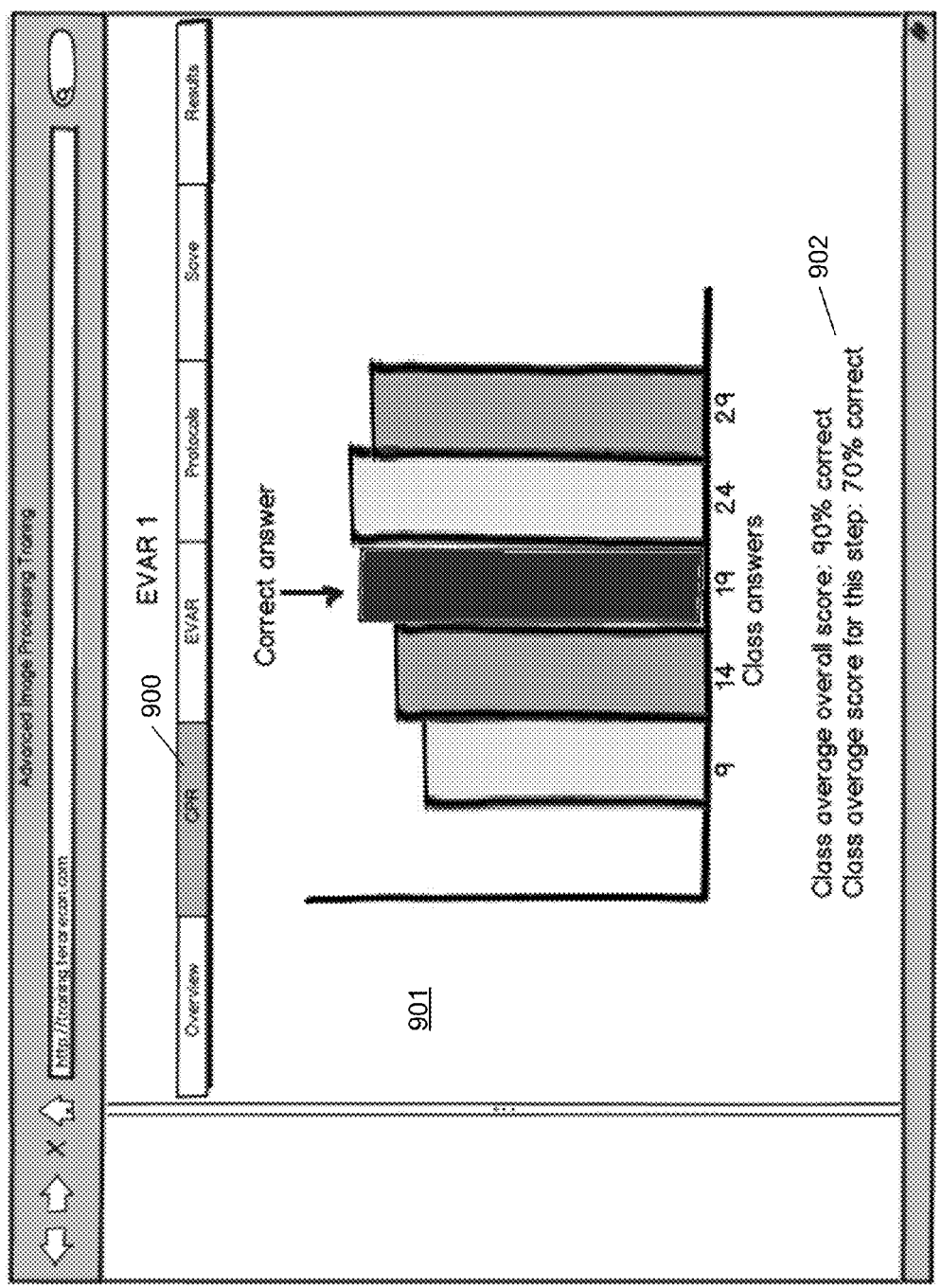
FIG. 9 is a screenshot illustrating a GUI of a class report according to one embodiment of the invention.

FIG. 9 is a screenshot illustrating a GUI of a class report according to one embodiment of the invention. This screen is showing the scores for CPR step of an EVAR 1 class. The step bar 900 shows which step is being summarized in the screen. A graph 901 shows the distribution of the class scores, as well as the correct score, so each student can see where his/her score compares to those of the rest of the class. The overall test results 902 are also shown. The overall test results include the results for all of the steps within the course.

In a more simplified setting, a course may consist of only one or a few simple questions, or steps. This type of course can be used in a classroom setting to poll the audience. For example, as part of a training course, an instructor may put a medical image on the screen and ask the people in the classroom to indicate what step they would take next. In this case, the instructor's "course" may only contain one multiple choice question which is answered in the classroom setting. The results can immediately be shown to the class in a manner similar to that shown in FIG. 9. This allows for a highly interactive and engaging instructional course.

The training system can be implemented on several different platforms. The system may be client-server based, cloud based (public or private), or local. The client for the system—the interface which the instructors and/or students use—may be internet browser based, mobile phone or tablet based, a proprietary thin or thick client, or other clients. Users may use a computer, mobile phone, tablet, or other access device to access the training system. The system may need to support a very large number of users, and may be local, regional, national or international in its reach. Access may be controlled by user type, or other ways.

According to some embodiments, medical training client software may be integrated with a medical image processing client software. Referring back to FIG. 1, for example, client 102 is a client which includes integrated image processing client software and training client software 112, which may be integrated medical software. In one embodiment, the integrated software integrates image(s) and/or image processing functionality with medical record software (MRS) and/or clinical trial software (CTS), which herein are collectively referred to as medical record and/or clinical software (MRCS). For example, imaging processing function may be implemented as integrated client 112 communicatively coupled to image processing server 101 over network 120. The integrated client 112 may be linked to medical software or embedded within the medical software.

The MRS is patient-centric software that focuses on medical records of the individual patients. Patient—centric means here that the software's primary purpose is to record and view data relating to the individual patient. This type of software may be referred to as electronic medical record (EMR) software, electronic health record (EHR) software, personal health record (PHR) software and other names. Information maintained by the MRS typically includes: patient ID, demographic, info—age, weight, height, Blood Pressure (BP), etc., lab orders and results, test orders and results, medical history, appointment history, appointments scheduled, exam history, prescriptions/medications, symptoms/diagnoses, and insurance/reimbursement information.

The CTS includes software for both retrospective and prospective clinical studies. This type of software may be referred to as a Clinical Trial Management System. CTS may also include software for research. CTS is trial-centric which means the primary purpose of the software is to collect and view aggregate data for multiple patients or participants. Although data is collected at the individual patient/participant level, this data is usually viewed "blindly". This means that the viewer and/or analyzer of the data generally do not know the identity of the individual patients/participants. However, data can be viewed at the individual patient/participant level where necessary. This is particularly important where images are involved. CTS typically includes: patient ID, concomitant medications, adverse events, randomization info, data collection, informed consent, aggregated data, and status of study.

In one embodiment, integrated client 112, which may be implemented as part of the integrated medical software executed within the client 102, displays medical information of a patient, including, e.g., the medical treatment history of a patient, which may be part of a medical record and/or trial record of the patient. Such records may be downloaded from a medical data server (not shown) over network 120 in response to a user request. In the case where the integrated medical software integrates MRS, the patient's full identity it typically displayed as part of the medical information. On the other hand, in the case of an integrated CTS, the patient is typically anonymous as discussed above, and the identity of the patient is typically not revealed as part of the displayed medical information.

In one embodiment, image(s) and/or image processing tools may be integrated with the integrated client 112. Integration can take the form of the image(s) and/or image processing tools showing up in the same window as the integrated client 112. Integration can also take the form of a window containing the image(s) and/or image processing tools opening up in a separate window from the MRCS window. It should be noted, however, that in either form of integration, the medical information of the patient and image(s) are displayed within the integrated medical software, without requiring the user of the integrated software to separately obtain the images via another software program.

In one embodiment, image processing tools 106 that are provided by the remote imaging processing server 101 are displayed to the user of the integrated client 112 executed on the client 102. In such an embodiment, the available image processing tools 106 are displayed in integrated client 112 as a set of graphical representations such as icons, which when activated by a user, allow an image to be manipulated by the remote imaging processing server 101. In one embodiment the image processing software is integrated with the MRCS program and also opens up "in context". "In context" means that the image processing software opens up to show the appropriate image(s) and/or tools for the current user and/or patient and/or affliction. The availability of imaging tools to a particular user depends on the access privileges of that particular user (e.g., doctors vs. medical students). Alternatively, the availability of imaging tools 106 may be determined based on a particular body part of a patient, which may be identified by certain tags such as DICOM tags.

For example, one doctor may prefer that the cardiovascular images for his patients open up in a 3D view, with vessel centerline tools available, yet the abdominal images for his patients open up in a coronal view with the flythrough, or virtual colonoscopy, tools available. He may prefer to have the other views and tools hidden from view. In another example, another doctor may prefer that the images for her patients open up showing the most recent views and tools that she used for that patient. In another example, the default view for cardiovascular cases may be set to show a particular view and tools, but the user may be able to change the default so that his/her preferences override the default views and tools.

In all of the above examples, ideally only the images that relate to the patient being evaluated at that time are able to be viewed. In addition, the user/physician does not need to search to find the images relating to the patient, the images are automatically associated with the correct patient, for example, based on the corresponding patient ID. To do this, the identity of the patient needs to be associated with the patient's images. This can be done by using tags, such as a common identifier, such as an ID number, metadata associated with one or more of the images, mining patient data, body part analysis, or other ways. Also, the appropriate tools need to be shown and inappropriate tools hidden. The tags are discussed in more details below. Note that images represent specific views of some of the images 105 rendered by image processing engine 104.

For example, an image or image series can be analyzed to determine whether it is a head, abdomen, or other body part, based on the anatomy. A skull has a characteristic shape, as do other parts of the anatomy. A catalog of reference images may be used to help identify specific body parts. Based on this analysis, the appropriate views and/or tools can be made visible to the user, and inappropriate views and/or tools can be hidden. For example, if the image series is of a head/skull, the image series may be shown in a certain view, such as an axial view, and tools associated with the brain visible. In addition, if certain key words, such as "tumor" or "stroke", are found in the MRCS record, specific tools may be shown, such as tools that detect a tumor or evaluate brain perfusion. It is also possible that a patient ID can be determined from the anatomy in an image based on shape, disease, tags etc. For example, an image of a dental area can be matched with dental records to identify a patient from medical images. Alternatively, an identifying tag can be included in the medical image—such as a tag with the patient ID number placed on or near the table of a CT scanner, or on the patient himself.

In another embodiment, the user of the software is able to customize how the image processing software is presented in context. For example, Doctor Y, a cardiologist, may prefer to have the images open up in a 3D model view, and have cardiology tool A and cardiology tool B visible to him. In this example, other views may be hidden (for example, the axial, sagittal, and coronal views) and other tools are hidden (for example, tools relating to the colon or the brain).

Figure 10A:
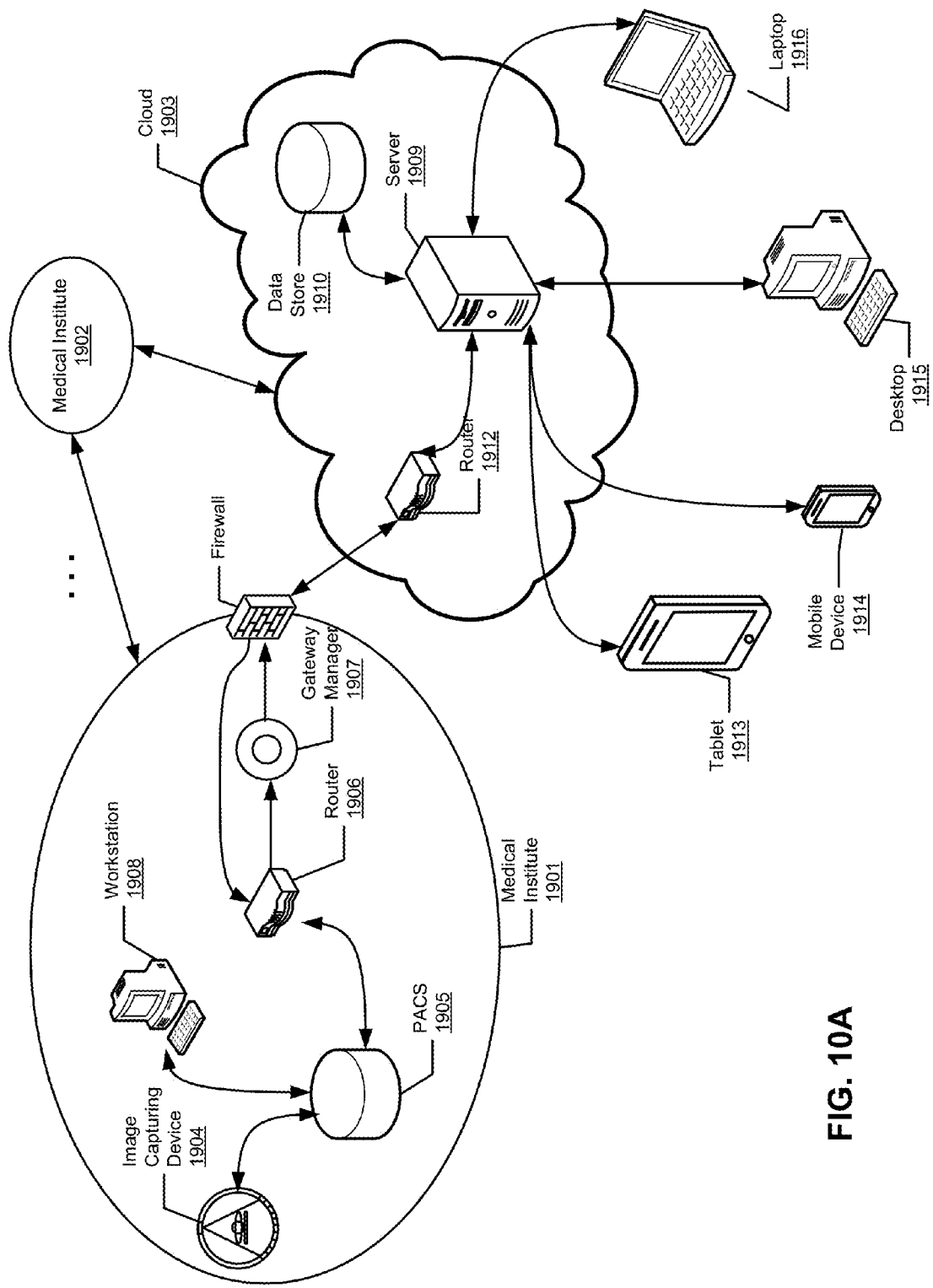
FIGS. 10A and 10b are block diagrams illustrating a cloud-based image processing system according to certain embodiments of the invention.
Figure 10B:
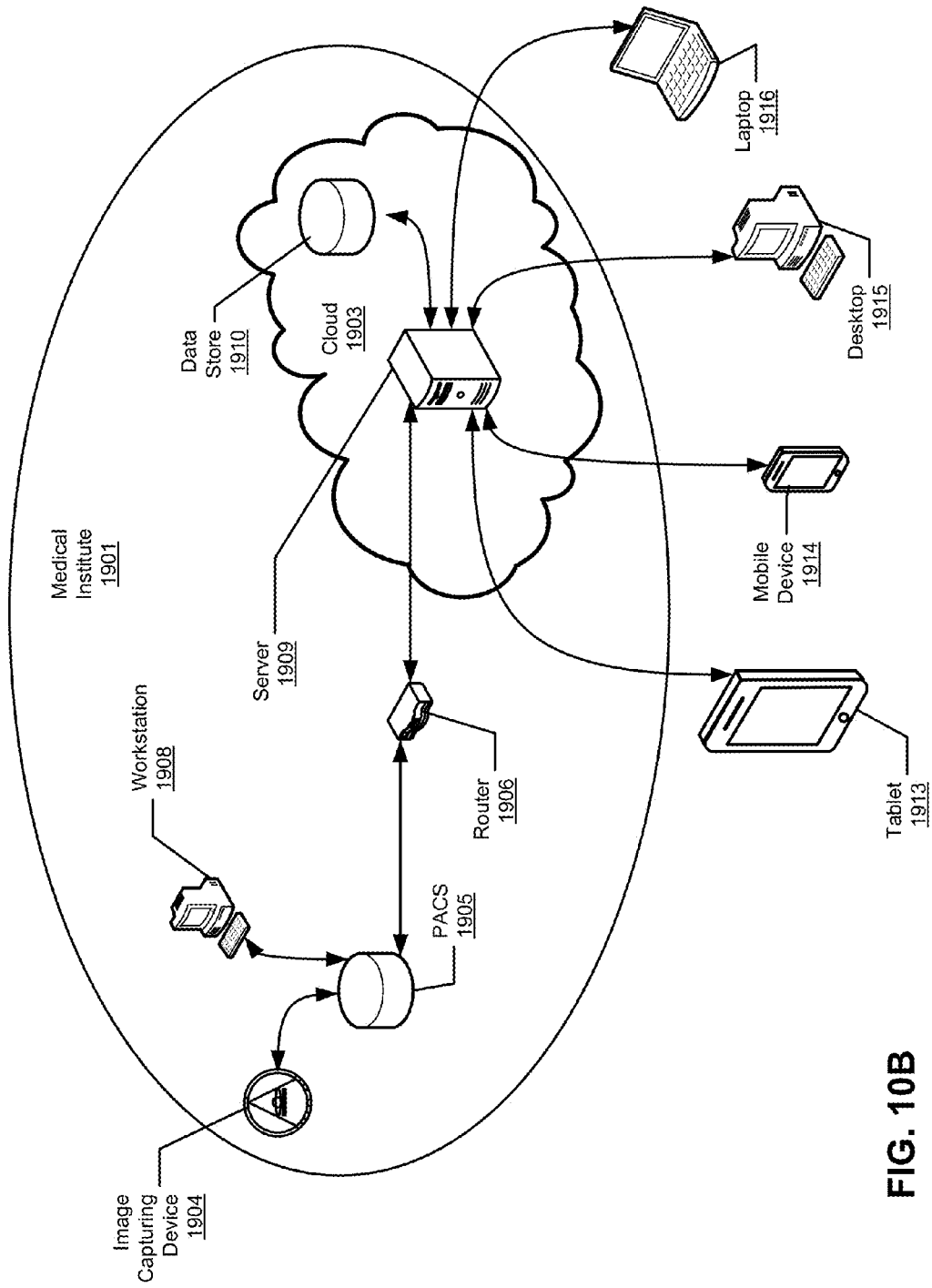

FIGS. 10A and 10b are block diagrams illustrating a cloud-based image processing system according to certain embodiments of the invention. Referring to FIG. 10A, according to one embodiment, system 1900 includes one or more entities or institutes 1901-1902 communicatively coupled to cloud 1903 over a network. Entities 1901-1902 may represent a variety of organizations such as medical institutes having a variety of facilities residing all over the world. For example, entity 1901 may include or be associated with image capturing device or devices 1904, image storage system (e.g., PACS) 1905, router 1906, and/or data gateway manager 1907. Image storage system 1905 may be maintained by a third party entity that provides archiving services to entity 1901, which may be accessed by workstation 1908 such as an administrator or user associated with entity 1901. Note that throughout this application, a medical institute is utilized as an example of an organization entity. However, it is not so limited; other organizations or entities may also be applied.

In one embodiment, cloud 1903 may represent a set of servers or clusters of servers associated with a service provider and geographically distributed over a network. For example, cloud 1903 may be associated with a medical image processing service provider such as TeraRecon of Foster City, Calif. A network may be a local area network (LAN), a metropolitan area network (MAN), a wide area network (WAN) such as the Internet or an intranet, or a combination thereof. Cloud 1903 can be made of a variety of servers and devices capable of providing application services to a variety of clients such as clients 1913-1916 over a network. In one embodiment, cloud 1903 includes one or more cloud servers 1909 to provide image processing services, one or more databases 1910 to store images and other medical data, and one or more routers 1912 to transfer data to/from other entities such as entities 1901-1902. If the cloud server consists of a server cluster, or more than one server, rules may exist which control the transfer of data between the servers in the cluster. For example, there may be reasons why data on a server in one country should not be placed on a server in another country.

Server 1909 may be an image processing server to provide medical image processing services to clients 1913-1916 over a network. For example, server 1909 may be implemented as part of a TeraRecon AquariusNET™ server and/or a TeraRecon AquariusAPS server. Data gateway manager 1907 and/or router 1906 may be implemented as part of a TeraRecon AquariusGATE device. Medical imaging device 1904 may be an image diagnosis device, such as X-ray CT device, MRI scanning device, nuclear medicine device, ultrasound device, or any other medical imaging device. Medical imaging device 1904 collects information from multiple cross-section views of a specimen, reconstructs them, and produces medical image data for the multiple cross-section views. Medical imaging device 1904 is also referred to as a modality.

Database 1910 may be a data store to store medical data such as digital imaging and communications in medicine (DICOM) compatible data or other image data. Database 1910 may also incorporate encryption capabilities. Database 1910 may include multiple databases and/or may be maintained by a third party vendor such as storage providers. Data store 1910 may be implemented with relational database management systems (RDBMS), e.g., Oracle™ database or Microsoft® SQL Server, etc. Clients 1913-1916 may represent a variety of client devices such as a desktop, laptop, tablet, mobile phone, personal digital assistant (PDA), etc. Some of clients 1913-1916 may include a client application (e.g., thin client application) to access resources such as medical image processing tools or applications hosted by server 1909 over a network. Examples of thin clients include a web browser, a phone application and others.

According to one embodiment, server 1909 is configured to provide advanced image processing services to clients 1913-1916, which may represent physicians from medical institutes, instructors, students, agents from insurance companies, patients, medical researchers, etc. Cloud server 1909, also referred to as an image processing server, has the capability of hosting one or more medical images and data associated with the medical images to allow multiple participants such as clients 1913-1916, to participate in a discussion/processing forum of the images in a collaborated manner or conferencing environment. Different participants may participate in different stages and/or levels of a discussion session or a workflow process of the images.

According to some embodiments, data gateway manager 1907 is configured to automatically or manually transfer medical data to/from data providers (e.g., PACS systems) such as medical institutes. Such data gateway management may be performed based on a set of rules or policies, which may be configured by an administrator or authorized personnel. In one embodiment, in response to updates of medical images data during an image discussion session or image processing operations performed in the cloud, the data gateway manager is configured to transmit over a network (e.g., Internet) the updated image data or the difference between the updated image data and the original image data to a data provider such as PACS 1905 that provided the original medical image data. Similarly, data gateway manager 1907 can be configured to transmit any new images and/or image data from the data provider, where the new images may have been captured by an image capturing device such as image capturing device 1904 associated with entity 1901. In addition, data gateway manager 1907 may further transfer data amongst multiple data providers that is associated with the same entity (e.g., multiple facilities of a medical institute). Furthermore, cloud 1903 may include an advanced preprocessing system (not shown) to automatically perform certain pre-processing operations of the received images using certain advanced image processing resources provided by the cloud systems. In one embodiment, gateway manager 1907 is configured to communicate with cloud 1903 via certain Internet ports such as port 80 or 443, etc. The data being transferred may be encrypted and/or compressed using a variety of encryption and compression methods. The term "Internet port" in this context could also be an intranet port, or a private port such as port 80 or 443 etc. on an intranet.

Figure 11:
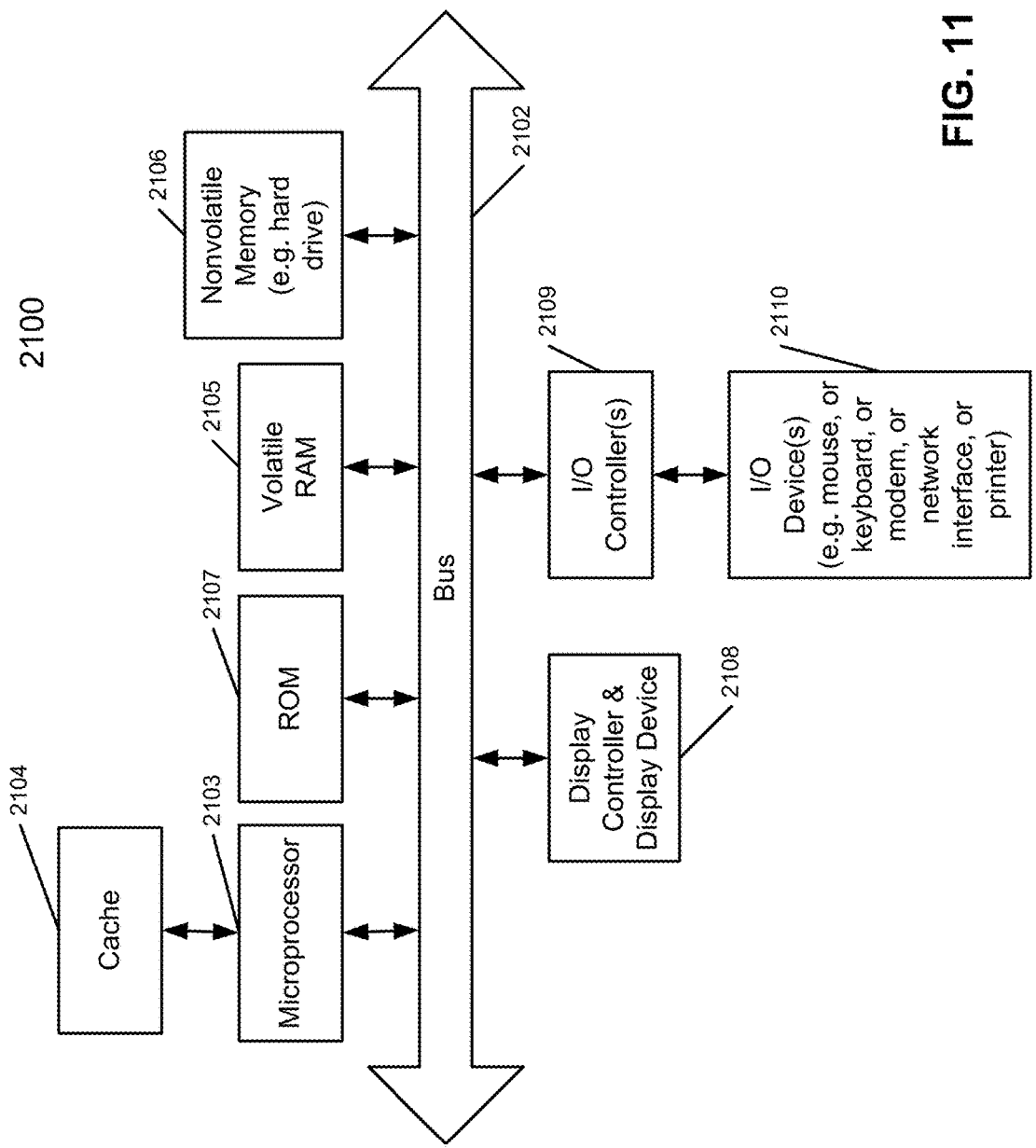
FIG. 11 is a block diagram of a data processing system, which may be used with one embodiment of the invention.

FIG. 11 is a block diagram of a data processing system, which may be used with one embodiment of the invention. For example, the system 2100 may be used as part of a server or a client as shown in FIGS. 10A and 10B. Note that while FIG. 11 illustrates various components of a computer system, it is not intended to represent any particular architecture or manner of interconnecting the components; as such details are not germane to the present invention. It will also be appreciated that network computers, handheld computers, cell phones and other data processing systems which have fewer components or perhaps more components may also be used with the present invention.

As shown in FIG. 11, the computer system 2100, which is a form of a data processing system, includes a bus or interconnect 2102 which is coupled to one or more microprocessors 2103 and a ROM 2107, a volatile RAM 2105, and a non-volatile memory 2106. The microprocessor 2103 is coupled to cache memory 2104. The bus 2102 interconnects these various components together and also interconnects these components 2103, 2107, 2105, and 2106 to a display controller and display device 2108, as well as to input/output (I/O) devices 2110, which may be mice, keyboards, modems, network interfaces, printers, and other devices which are well-known in the art.

Typically, the input/output devices 2110 are coupled to the system through input/output controllers 2109. The volatile RAM 2105 is typically implemented as dynamic RAM (DRAM) which requires power continuously in order to refresh or maintain the data in the memory. The non-volatile memory 2106 is typically a magnetic hard drive, a magnetic optical drive, an optical drive, or a DVD RAM or other type of memory system which maintains data even after power is removed from the system. Typically, the non-volatile memory will also be a random access memory, although this is not required.

While FIG. 11 shows that the non-volatile memory is a local device coupled directly to the rest of the components in the data processing system, the present invention may utilize a non-volatile memory which is remote from the system; such as, a network storage device which is coupled to the data processing system through a network interface such as a modem or Ethernet interface. The bus 2102 may include one or more buses connected to each other through various bridges, controllers, and/or adapters, as is well-known in the art. In one embodiment, the I/O controller 2109 includes a USB (Universal Serial Bus) adapter for controlling USB peripherals. Alternatively, I/O controller 2109 may include an IEEE-1394 adapter, also known as FireWire adapter, for controlling FireWire devices.

A course may comprise one case, for example a lung cancer, cardiovascular disease, colon, breast, or other type of case. A course may also comprise multiple cases, either of the same type, or multiple types. A course may or may not incorporate testing. Test results of a course may be used to grade or score a student, or may be used for a student's learning only. Each case within a course may incorporate several steps. For example, a case may involve finding several colon polyps or lung nodules. In addition, a course may ask the student to measure the polyps/nodules. In addition, a course may ask the student to make an assessment of the various polyps/nodules. Where multiple steps and or locating of polyps/nodules/tumors/etc. is part of the course, the student's score may depend on how accurately the student finds the various artifacts and also how many he finds.

If a course comprises more than one case, the progress of the case, visible to the student and/or the instructor, may show how many of the required cases have been adequately completed. A course may also implement a logic tree. For example, a student may be asked to evaluate symptoms, which may involve imaging, and based on the symptoms, conclude possible conclusions. See FIG. 22 for an example logic tree.

In one embodiment, a course may utilize an image database that contains a pre-requisite number of cases that the student has to complete in a specific time period to get certification to be able to read such cases. These courses are usually self-paced and students are given the entire number of studies to review at their own pace or are given specific cases to read in a specified time period. The instructor has pre prepared clinical reports with model answers in a clinical report. In the review of these cases, the students experience within the course emulates a true clinical reading room interpretation process where a user uses the necessary tools to arrive at a clinical interpretation of the study. The tools available to the student in this embodiment may be the same tools available to a user in a non-course situation, in other words, the student may be required to choose the correct tool or tools from among more than one tool to properly complete the course requirements. The student is asked to do what is needed to complete the cases. For example the student may be asked to detect polyps, identify quantify, and/or measure stenoses, measure/quantify global ejection fraction, determine a standard uptake value, locate tumors and/or take other measurements. Key images or screenshots are provided where appropriate. After the student submits his results, he may receive instant feedback, including the model answers, of the current study, so he can compare his results to the instructor's result. The model answer may include images, anatomical identification, measurements, etc.

In one embodiment, a student's work is tracked and saved in image meta-data which is associated only with that student. This allows each student to review his work and for an instructor to review the steps taken and results for each student individually. An instructor can also review and/or compare the work of more than one or all of his students.

The embodiments described above can be applied to a variety of medical areas. For example, the techniques described above can be applied to vessel analysis (including Endovascular Aortic Repair (EVAR) and electrophysiology (EP) planning). Such vessel analysis is performed for interpretation of both coronary and general vessel analysis such as carotid and renal arteries, in addition to aortic endograft and electro-physiology planning. Tools provided as cloud services include auto-centerline extraction, straightened view, diameter and length measurements, Curved Planar Reformation (CPR) and axial renderings, as well as charting of the vessel diameter vs. distance and cross-sectional views. The vessel track tool provides a Maximum Intensity Projection (MIP) view in two orthogonal planes that travels along and rotates about the vessel centerline for ease of navigation and deep interrogation. Plaque analysis tools provide detailed delineation of non luminal structure such as soft plaque, calcified plaque and intra-mural lesions.

In addition, the techniques described above can be utilized in the area of endovascular aortic repair. According to some embodiments, vascular analysis tools provided as cloud services support definition of report templates which captures measurements for endograft sizing. Multiple centerlines can be extracted to allow for planning of EVAR procedures with multiple access points. Diameters perpendicular to the vessel may be measured along with distances along the two aorto-iliac paths. Custom workflow templates may be used to enable the major aortic endograft manufactures' measurement specifications to be made as required for stent sizing. Sac segmentation and volume determination with a "clock-face" overlay to aid with documenting the orientation and location of branch vessels for fenestrated and branch device planning, may also be used. Reports containing required measurements and data may be generated.

The techniques described above can also be applied in the left atrium analysis mode, in which semi-automated left atrium segmentation of each pulmonary vein ostium is supported with a single-click distance pair tool, provided as cloud services, for assessment of the major and minor vein diameter. Measurements are automatically detected and captured into the integrated reporting system. These capabilities can be combined with other vessel analysis tools to provide a comprehensive and customized EP planning workflow for ablation and lead approach planning.

The techniques described above can also be utilized in calcium scoring. Semi-automated identification of coronary calcium is supported with Agatston, volume and mineral mass algorithms being totaled and reported on-screen. Results may be stored in an open-format database along with various other data relating to the patient and their cardiovascular history and risk factors. A customized report can be automatically generated, as part of cloud services, based upon these data. Also includes report generation as defined by the Society of Cardiovascular Computed Tomography (SCCT) guidelines.

The techniques described above can also be utilized in a time-volume analysis (TVA), which may include fully-automated calculation of left ventricular volume, ejection fraction, myocardial volume (mass) and wall thickening from multi-phasic data. A fast and efficient workflow provided as part of cloud services allows for easy verification or adjustment of levels and contours. The results are presented within the integrated reporting function.

The techniques described above can also be utilized in the area of segmentation analysis and tracking (SAT), which includes supports analysis and characterization of masses and structures in various scans, including pulmonary CT examinations. Features include single-click segmentation of masses, manual editing tools to resolve segmentation issues, automatic reporting of dimensions and volume, graphical 3D display of selected regions, integrated automated reporting tool, support for follow-up comparisons including percent volume change and doubling time, and support for review of sphericity filter results.

The techniques described above can also be utilized in the area of flythrough which may include features of automatic segmentation and centerline extraction of the colon, with editing tools available to redefine these centerlines if necessary. 2D review includes side-by-side synchronized supine and prone data sets in either axial, coronal or sagittal views with representative synchronized endoluminal views. 3D review includes axial, coronal and sagittal MPR or MIP image display with large endoluminal view and an unfolded view that displays the entire colon. Coverage tracking is supported to ensure 100% coverage with stepwise review of unviewed sections, one-click polyp identification, bookmark and merge findings, as well as a cube view for isolating a volume of interest and an integrated contextual reporting tool. Support is provided for use of sphericity filter results.

The techniques described above can also be utilized in the area of time-dependent analysis (TDA), which provides assessment tools for analyzing the time-dependent behavior of appropriate computerized tomographic angiography (CTA) and/or MRI examinations, such as within cerebral perfusion studies. Features include support for loading multiple time-dependent series at the same time, and a procedural workflow for selecting input and output function and regions of interest. An integrated reporting tool is provided as well as the ability to export the blood flow, blood volume and transit time maps to DICOM. The tools may also be used with time-dependent MR acquisitions to calculate various time-dependent parameters.

The techniques described above can also be utilized in the area of CTA-CT subtraction, which includes automatic registration of pre- and post-contrast images, followed by subtraction or dense-voxel masking technique which removes high-intensity structures (like bone and surgical clips) from the CTA scan without increasing noise, and leaving contrast-enhanced vascular structures intact.

The techniques described above can also be utilized in dental analysis, which provides a CPR tool which can be applied for review of dental CT scans, offering the ability to generate "panoramic" projections in various planes and of various thicknesses, and cross-sectional MPR views at set increments along the defined curve plane.

The techniques described above can also be utilized in the area of multi-phase MR (basic, e.g. breast, prostate MR). Certain MR examinations (for example, breast, prostate MR) involve a series of image acquisitions taken over a period of time, where certain structures become enhanced over time relative to other structures. This module features the ability to subtract a pre-enhancement image from all post-enhancement images to emphasize visualization of enhancing structures (for example, vascular structures and other enhancing tissue). Time-dependent region-of-interest tools are provided to plot time-intensity graphs of a given region.

The techniques described above can also be utilized in parametric mapping (e.g. for multi-phase Breast MR), in which the parametric mapping module pre-calculates overlay maps where each pixel in an image is color-coded depending on the time-dependent behavior of the pixel intensity. The techniques described above can also be utilized in the area of SphereFinder (e.g. sphericity filter for lung and colon). SphereFinder pre-processes datasets as soon as they are received and applies filters to detect sphere-like structures. This is often used with lung or colon CT scans to identify potential areas of interest. The techniques described can also be utilized in fusion for CT/MR/PET/SPECT. Any two CT, PET, MR or SPECT series, or any two-series combination can be overlaid with one assigned a semi-transparent color coding and the other shown in grayscale and volume rendering for anatomical reference. Automatic registration is provided and subtraction to a temporary series or to a saved, third series is possible.

The techniques described above can also be utilized in the area of Lobular Decomposition. Lobular Decomposition is an analysis and segmentation tool that is designed with anatomical structures in mind. For any structure or organ region which is intertwined with a tree-like structure (such as an arterial and/or venous tree), the Lobular Decomposition tool allows the user to select the volume of interest, as well as the trees related to it, and to partition the volume into lobes or territories which are most proximal to the tree or any specific sub-branch thereof. This generic and flexible tool has potential research applications in analysis of the liver, lung, heart and various other organs and pathological structures.

The techniques described above can also be utilized in the area of Volumetric Histogram. Volumetric Histogram supports analysis of a given volume of interest based on partition of the constituent voxels into populations of different intensity or density ranges. This can be used, for example, to support research into disease processes such as cancer (where it is desirable to analyze the composition of tumors, in an attempt to understand the balance between active tumor, necrotic tissue, and edema), or emphysema (where the population of low-attenuation voxels in a lung CT examination may be a meaningful indicator of early disease).

The techniques described above can also be utilized in the area of Motion Analytics. Motion Analytics provides a powerful 2D representation of a 4D process, for more effective communication of findings when interactive 3D or 4D display is not available. Any dynamic volume acquisition, such as a beating heart, can be subjected to the Motion Analysis, to generate a color-coded "trail" of outlines of key boundaries, throughout the dynamic sequence, allowing a single 2D frame to capture and illustrate the motion, in a manner that can be readily reported in literature. The uniformity of the color pattern, or lack thereof, reflects the extent to which motion is harmonic, providing immediate visual feedback from a single image.

The techniques described above can also be utilized to support other areas such as Multi-KV, enhanced multi-modality, findings workflow, and iGENTLE available from TeraRecon. Multi-KV: Support for Dual Energy and Spectral Imaging provides support for established applications of dual energy or spectral imaging CT data, such as removal of bone or contrast, as well as toolkits to support research and investigation of new applications of such imaging techniques. Enhanced multi-modality support is offered, including support for PET/MR fusion, and improved applications for MR such as time-intensity analysis and parametric mapping tools, which may be applied in the study of perfusion characteristics of normal or cancerous tissue.

The techniques described above can also be utilized in the area of Findings Workflow. Findings Workflow supports progressive analysis of serial acquisitions, for the same patient. Each finding can be tracked across multiple examinations, in a table that is maintained indefinitely in the system's database, without requiring the prior scans to remain present on the system. Measurement data and key images are captured and retained, allowing new scans to be placed in context with prior results, and reports to be produced at any time. Support for RECIST 1.1 is included although the tool may readily be used for analysis of various progressive conditions, not only those related to oncology. Export using the AIM (Annotation and Image Markup) XML Schema is supported.

The techniques described above can also be utilized in the area of iGENTLE. iGENTLE ensures that the system's powerful suite of segmentation, centerline, and metadata extraction tools continue to work effectively, even with noisy scans characterized by low-dose acquisitions. Metadata are extracted from enhanced copies of the original scan, and then applied back onto the original, unmodified data, to improve performance of 3D tools without denying access to the original scan data.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as those set forth in the claims below, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Embodiments of the invention also relate to an apparatus for performing the operations herein. Such a computer program is stored in a non-transitory computer readable medium. A machine-readable medium includes any mechanism for storing information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices).

The processes or methods depicted in the preceding figures may be performed by processing logic that comprises hardware (e.g. circuitry, dedicated logic, etc.), software (e.g., embodied on a non-transitory computer readable medium), or a combination of both. Although the processes or methods are described above in terms of some sequential operations, it should be appreciated that some of the operations described may be performed in a different order. Moreover, some operations may be performed in parallel rather than sequentially.

Embodiments of the present invention are not described with reference to any particular programming language. It will be appreciated that a variety of programming languages may be used to implement the teachings of embodiments of the invention as described herein.

In the foregoing specification, embodiments of the invention have been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A method for providing a networked system of computer training stations, the method comprising:
   providing an image processing server that includes an image processing training system, the image processing training system having at least one medical image associated with a medical image processing training course (MIPTC), including:
      capturing the at least one medical image by a medical imaging device so that the at least one medical image includes a view of an internal organ or structure of a body captured by the medical imaging device in image slices that are combined to form the at least one medical image, and
      storing the at least one medical image by a storage associated with the image processing server;
   providing a first computer training station, the first computer training station implemented by a first client device and a first display, including:
      displaying by the first client device, in a first display area of the first display, the at least one medical image stored by the storage associated with the image processing server,
      providing, by the first client device within a second display area of the first display, a first workflow template of a plurality of workflow templates stored in the image processing server:
         wherein the first workflow template is provided based on a role or an access privilege of a first user,
         wherein the first workflow template comprises a representation of a predefined set of workflow stages associated with a type of medical diagnosis or processing, and
         wherein each workflow stage defines one or more image processing operations and includes one or more user selectable image processing tools to allow users to measure a diameter, an area, a distance, or a volume of a body part within the medical image displayed in the first display area,
      providing, by the first client device, an instruction associated with a currently displayed workflow stage of the first workflow template, the instruction requesting the first user to perform a quantitative determination on at least a portion of the body part within the medical image displayed in the first display area and to perform the one or more image processing operations on the medical image using the one or more user selectable image processing tools provided by the currently displayed workflow stage on the first client device,
      transmitting, from the first client device to the image processing server, a user action input performed by the first user using the one or more of the image processing tools in response to performing the requested quantitative determination and the one or more image processing operations, wherein the user action invokes the image processing server to perform the quantitative determination based on a determined type of user action performed by the first user, receiving, by the first client device from the image processing server, a quantitative value as a result of the image processing server performing the quantitative determination, and comparing, by the first client device, the quantitative value to a predefined model answer associated with the medical image to determine a score evaluating the quantitative determination performed by the first user, and displaying, by the first client device, the score on the first display; and, providing a second computer training station, the second computer training station implemented by a second client device and a second display, including:

providing, by the second client device and within a second display area of the first display, a second workflow template of the plurality of workflow templates stored in the image processing server, wherein the second workflow template is provided based on a role or an access privilege of a second user.

2. The method of claim 1, further comprising displaying the quantitative value representing the result of the user action compared to the predefined model answer.

3. The method of claim 1, wherein the quantitative determination is a two-dimensional (2D) image measurement.

4. The method of claim 1, wherein the quantitative determination is a three-dimensional (3D) image measurement.

5. The method of claim 1, wherein the predefined model answer comprises a predetermined range, and wherein the predetermined range is one of a plurality of predefined ranges, each associated with one of a plurality different training levels.

6. The method of claim 1, wherein the instruction further requests the first user to locate and identify the body part from the displayed image.

7. The method of claim 6, wherein the instruction further requests the first user to isolate a volume of anatomy for evaluation, wherein the anatomy represent one of a bone, an organ, a blood vessel, a colon, a tumor, a nodule, and a polyp.

8. The method of claim 1, wherein the instruction comprises determining one of an ejection fraction, an uptake value and a flow measurement.

9. The method of claim 1, further comprising:

aggregating quantitative determination answers of the first user with answers from other users who have taken the training course previously; and displaying a statistics result based on the aggregated answers.

10. A system comprising:

an image processing server that includes an image processing training system, the image processing training system having at least one medical image associated with a medical image processing training course (MIPTC);

a medical imaging device configured to capture the at least one medical image and store the at least one medical image in a storage associated with the image processing server, wherein the at least one medical image includes a view of an internal organ or structure of a body captured by the medical imaging device, the medical imaging device configured to capture and combine image slices to form the at least one medical image;

a first computer training station, the first computer training station implemented by a first client device and a first display:

wherein the first client device is configured to display, in a first display area of the first display, the at least one medical image stored by the storage associated with the image processing server, wherein the first client device is configured to provide within a second display area of the first display, a first workflow template of a plurality of workflow templates stored in the image processing server, wherein the first workflow template is provided based on a role or an access privilege of a first user, wherein the first workflow template comprises a representation of a predefined set of workflow stages associated with a type of medical diagnosis or processing, wherein each workflow stage defines one or more image processing operations and includes one or more user selectable image processing tools to allow users to measure a diameter, an area, a distance, or a volume of a body part within the medical image displayed in the first display area, wherein the first client device is configured to provide an instruction associated with a currently displayed workflow stage of the first workflow template, the instruction requesting the first user to perform a quantitative determination on at least a portion of the body part within the medical image displayed in the first display area and to perform the one or more image processing operations on the medical image using the one or more user selectable image processing tools provided by the currently displayed workflow stage on the first client device, wherein the first client device is configured to transmit to the image processing server, a user action input performed by the first user using the one or more of the user selectable image processing tools in response to performing the requested quantitative determination and the one or more image processing operations, wherein the user action invokes the image processing server to perform the quantitative determination based on a determined type of user action performed by the first user, wherein the first client device is configured to receive from the image processing server, a quantitative value as a result of the image processing server performing the quantitative determination, and wherein the quantitative value is compared to a predefined model answer associated with the medical image to determine a score evaluating the quantitative determination performed by the first user, and displaying the score on the first display; and, a second computer training station, the second computer training station implemented by a second client device and a second display:

wherein the second client device is configured to provide within a second display area of the first display, a second workflow template of the plurality of workflow templates stored in the image processing server, wherein the second workflow template is provided based on a role or an access privilege of a second user.

11. The system of claim 10, wherein the method further comprises displaying the quantitative value representing the result of the user action compared to the predefined model answer.

12. The system of claim 10, wherein the quantitative determination is a two-dimensional (2D) image measurement.

13. The system of claim 10, wherein the quantitative determination is a three-dimensional (3D) image measurement.

14. The system of claim 10, wherein the predefined model answer comprises a predetermined range, and wherein the predetermined range is one of a plurality of predefined ranges, each associated with one of a plurality different training levels.

15. The system of claim 10, wherein the instruction further requests the first user to locate and identify the body part from the displayed image.

16. The system of claim 15, wherein the instruction further requests the first user to isolate a volume of anatomy for evaluation, wherein the anatomy represent one of a bone, an organ, a blood vessel, a colon, a tumor, a nodule, and a polyp.

17. The system of claim 10, wherein the instruction comprises determining one of an ejection fraction, an uptake value and a flow measurement.

18. The system of claim 10, wherein quantitative determination answers of the first user are aggregated with answers from other users who have taken the training course previously and a statistics result is displayed based on the aggregated answers.

19. A method for providing a networked system of computer training stations, the method comprising:
providing software stored on non-transitory computer readable medium that when run on an image processing server implements an image processing training system, the image processing training system having at least one medical image associated with a medical image processing training course (MIPTC), wherein the at least one medical image includes a view of an internal organ or structure of a body captured by a medical imaging device in image slices that are combined to form the at least one medical image, including:
capturing the at least one medical image by the medical imaging device, and
storing the at least one medical image in a storage associated with the image processing server; and,
providing software stored on non-transitory computer readable medium that when run on a first computer training station that includes a first client device and a first display, causes the first client device to perform the following:
displaying by the first client device, in a first display area of the first display, the at least one medical image stored in the image processing server, and
providing, by the first client device within a second display area of the first display, a first workflow template of a plurality of workflow templates stored in the image processing server:
wherein the first workflow template is provided based on a role or an access privilege of a first user,
wherein the first workflow template comprises a representation of a predefined set of workflow stages associated with a type of medical diagnosis or processing, and
wherein each workflow stage defines one or more image processing operations and includes one or more user selectable image processing tools to allow users to measure a diameter, an area, a distance, or a volume of a body part within the medical image displayed in the first display area,
providing, by the first client device, an instruction associated with a currently displayed workflow stage of the first workflow template, the instruction requesting the first user to perform a quantitative determination on at least a portion of the body part within the medical image displayed in the first display area and to perform the one or more user selectabe image processing operations on the medical image using the one or more image processing tools provided by the currently displayed workflow stage on the first client device,
transmitting, from the first client device to the image processing server, a user action input performed by the first user using the one or more of the user selectable image processing tools in response to performing the requested quantitative determination and the one or more image processing operations, wherein the user action invokes the image processing server to perform the quantitative determination based on a determined type of user action performed by the first user,
receiving, by the first client device from the image processing server, a quantitative value as a result of the image processing server performing the quantitative determination, and
comparing the quantitative value to a predefined model answer associated with the medical image to determine a score evaluating the quantitative determination performed by the first user, and
displaying, by the first client device, the score on the first display.

20. The method of claim 19, further comprising displaying the quantitative value representing the result of the user action compared to the predefined model answer.

21. The method of claim 19, wherein the quantitative determination is a two-dimensional (2D) image measurement.

22. The method of claim 19, wherein the quantitative determination is a three-dimensional (3D) image measurement.

23. The method of claim 19, wherein the predefined model answer comprises a predetermined range, and wherein the predetermined range is one of a plurality of predefined ranges, each associated with one of a plurality different training levels.

24. The method of claim 19, wherein the instruction further requests the first user to locate and identify the body part from the displayed image.

25. The method of claim 24, wherein the instruction further requests the first user to isolate a volume of anatomy for evaluation, wherein the anatomy represent one of a bone, an organ, a blood vessel, a colon, a tumor, a nodule, and a polyp.

26. The method of claim 19, wherein the instruction comprises determining one of an ejection fraction, an uptake value and a flow measurement.

27. The method of claim 19, further comprising:
aggregating quantitative determination answers of the first user with answers from other users who have taken the training course previously; and displaying a statistics result based on the aggregated answers.

* * * * *